United States Patent
Parker et al.

(10) Patent No.: US 8,912,338 B2
(45) Date of Patent: *Dec. 16, 2014

(54) PESTICIDAL COMPOSITIONS

(71) Applicant: Dow AgroSciences LLC, Indianapolis, IN (US)

(72) Inventors: Marshall H. Parker, Carmel, IN (US); Maurice C. Yap, Zionsville, IN (US); Joseph D. Eckelbarger, Carmel, IN (US); Ann M. Buysse, Carmel, IN (US); Jonathan M. Babcock, Carmel, IN (US); Ricky Hunter, Westfield, IN (US); Yelena Adelfinskaya, Carmel, IN (US); Jack G. Samaritoni, Avon, IN (US); Negar Garizi, Westfield, IN (US); Tony K. Trullinger, Westfield, IN (US)

(73) Assignee: Dow AgroScience, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,407

(22) Filed: Nov. 1, 2013

(65) Prior Publication Data
US 2014/0057785 A1    Feb. 27, 2014

Related U.S. Application Data

(63) Continuation of application No. 13/219,746, filed on Aug. 29, 2011, now Pat. No. 8,604,211.

(60) Provisional application No. 61/378,528, filed on Aug. 31, 2010.

(51) Int. Cl.
| | | |
|---|---|---|
| *C07D 409/00* | (2006.01) | |
| *A01N 43/82* | (2006.01) | |
| *A01N 47/12* | (2006.01) | |
| *A01N 47/18* | (2006.01) | |
| *A01N 47/40* | (2006.01) | |
| *A01N 53/00* | (2006.01) | |
| *A01N 55/00* | (2006.01) | |
| *C07D 417/04* | (2006.01) | |

(52) U.S. Cl.
CPC ............ *A01N 43/82* (2013.01); *A01N 47/12* (2013.01); *A01N 47/18* (2013.01); *A01N 47/40* (2013.01); *A01N 53/00* (2013.01); *A01N 55/00* (2013.01); *C07D 417/04* (2013.01)
USPC ..................................................... 546/279.7

(58) Field of Classification Search
CPC ................................................... C07D 417/04
See application file for complete search history.

(56) References Cited

U.S. PATENT DOCUMENTS

| | | | |
|---|---|---|---|
| 4,151,167 A | 4/1979 | Kirkpatrick | |
| 2002/0013326 A1 | 1/2002 | Tiebes et al. | |
| 2009/0163545 A1* | 6/2009 | Goldfarb | 514/312 |

FOREIGN PATENT DOCUMENTS

| | | | |
|---|---|---|---|
| WO | WO2009/045761 A1 | 4/2009 | |
| WO | WO 2009045761 A1 * | 4/2009 | |
| WO | PCT/US2011/049475 | 1/2012 | |

OTHER PUBLICATIONS

Adv. Drug Deliv. Rev. 2001, vol. 48, pp. 3-26.*
Studies on Pyridine Derivatives. IX.Synthesis and Herbicidal Activities of N-( 1-Carbomethoxy)-ethyl-N-[ 5-( 2-chloropyrid-4-yl) -1, 3, 4-thiodiazol-2-yl] Amides, Chao, et al., Chinese Journal of Pesticide Science, 2004, 6(3):15-20.
Crystalline Solids, Vippagunta, et al., Advanced Drug Delivery Reviews 48 (2001) 3-26.
The Organic Chemistry of Drug Design and Drug Action, Richard B. Silverman, Elsevier Academic Press, Second Edition, pp. 29-32.

* cited by examiner

*Primary Examiner* — Heidi Reese
(74) *Attorney, Agent, or Firm* — Carl D. Corvin

(57) ABSTRACT

Molecules according to Formula One:

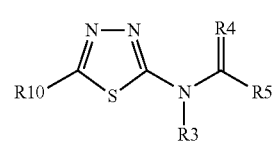

Formula One wherein R10 is selected from the following

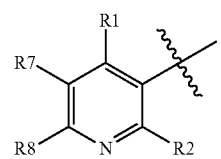

(a)

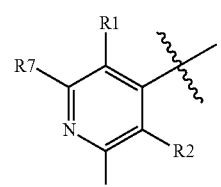

(b)

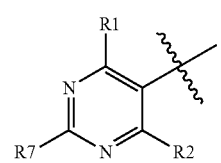

(c)

are provided. Furthermore, pesticidal compositions that comprise these molecules, and processes related to their uses as pesticides are disclose.

10 Claims, No Drawings

PESTICIDAL COMPOSITIONS

CROSS-REFERENCE TO RELATED APPLICATIONS

This application is a continuation of U.S. non-provisional application Ser. No. 13/219,746, filed Aug. 29, 2011, now allowed, which claims the benefit of U.S. provisional application 61/378,528, filed Aug. 31, 2010. The entire contents of these prior applications is hereby incorporated by reference into this application.

FIELD OF THE INVENTION

The invention disclosed in this document is related to the field of processes to produce molecules that are useful as pesticides (e.g., acaricides, insecticides, molluscicides, and nematicides), such molecules, and processes of using such molecules to control pests.

BACKGROUND OF THE INVENTION

Pests cause millions of human deaths around the world each year. Furthermore, there are more than ten thousand species of pests that cause losses in agriculture. The worldwide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Acaricide Group" is defined under the heading "ACARICIDES".

"AI Group" is defined after the place in this document where the "Herbicide Group" is defined.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Fungicide Group" is defined under the heading "FUNGICIDES."

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Herbicide Group" is defined under the heading "HERBICIDES."

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

"Insecticide Group" is defined under the heading "INSECTICIDES."

"Nematicide Group" is defined under the heading "NEMATICIDES"

"Synergist Group" is defined under the heading "SYNERGISTIC MIXTURES AND SYNERGISTS"

DETAILED DESCRIPTION OF THE INVENTION

This document discloses molecules having the following formula ("Formula One"):

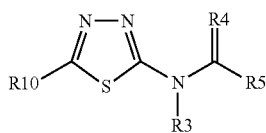

Formula One wherein
R10 is selected from the following group

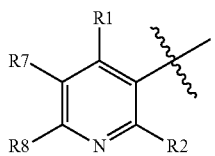
(a)

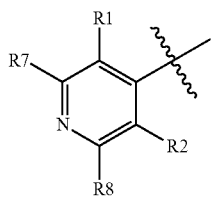
(b)

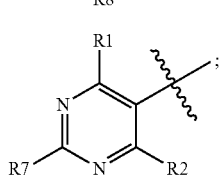
(c)

R1 is selected from H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

R3 is H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl)S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9;

wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

R4 is O, S, NR9, or NOR9;
R5 is
($C_1$-$C_{12}$ alkenyl)S(O)$_n$($C_1$-$C_{12}$ alkyl),
($C_1$-$C_{12}$ alkyl(R6))S(O)$_n$($C_1$-$C_{12}$ alkyl),
($C_1$-$C_{12}$ alkyl)(S($C_1$-$C_{12}$ alkyl(each independent from the other)))$_2$,
($C_1$-$C_{12}$ alkyl)C(=NO($C_1$-$C_{12}$ alkyl))($C_1$-$C_{12}$ alkyl),
($C_1$-$C_{12}$ alkyl)C(=O)($C_1$-$C_{12}$ alkyl),
($C_1$-$C_{12}$ alkyl)C(=O)O($C_1$-$C_{12}$ alkyl),
($C_1$-$C_{12}$ alkyl)N(R9)$_2$,
($C_1$-$C_{12}$ alkyl)N(R9)C(=O)O($C_1$-$C_{12}$ alkyl),
($C_1$-$C_{12}$ alkyl)N(R9)C(=O)O($C_1$-$C_{12}$ alkyl)R6,
($C_1$-$C_{12}$ alkyl)O($C_1$-$C_{12}$ alkyl),
($C_1$-$C_{12}$ alkyl)OC(=O)($C_1$-$C_{12}$ alkyl)S(O)$_n$($C_1$-$C_{12}$ alkyl),
($C_1$-$C_{12}$ alkyl)OSi(($C_1$-$C_{12}$ alkyl)$_3$ each independent from the other),
($C_1$-$C_{12}$ alkyl)S(O)$_n$($C_1$-$C_{12}$ haloalkyl),
($C_1$-$C_{12}$ alkyl)S(O)$_n$(=NCN)($C_1$-$C_{12}$ alkyl),
($C_1$-$C_{12}$ alkyl)S(O)$_n$($C_1$-$C_{12}$ alkenyl),
($C_1$-$C_{12}$ alkyl)S(O)$_n$($C_1$-$C_{12}$ alkyl),
($C_3$-$C_{12}$ cycloalkyl)($C_1$-$C_{12}$ alkyl)(S(O)$_n$($C_1$-$C_{12}$ alkyl),
($C_1$-$C_{12}$ alkyl)S(O)$_n$($C_1$-$C_{12}$ alkyl)R6,
($C_1$-$C_{12}$ alkyl)S(O)$_n$($C_6$-$C_{20}$ aryl),
($C_1$-$C_{12}$ alkyl)S(O)$_n$R6,
($C_1$-$C_{12}$ alkyl)S(O)$_n$C(=O)($C_1$-$C_{12}$ alkyl),
($C_1$-$C_{12}$ alkylCN)S(O)$_n$($C_1$-$C_{12}$ alkyl),
($C_1$-$C_{12}$ alkylN(R9)$_2$)S(O)$_n$($C_1$-$C_{12}$ alkyl), N(R9)(C$_1$-C$_{12}$ alkyl)O(C$_1$-C$_{12}$ alkyl),
N(R9)(C$_1$-C$_{12}$ alkyl)S(O)$_n$(C$_1$-C$_{12}$ alkyl),
O(C$_1$-C$_{12}$ alkyl),
O(C$_1$-C$_{12}$ alkyl)O(C$_1$-C$_{12}$ alkyl),
O(C$_1$-C$_{12}$ alkyl)S(O)$_n$(C$_1$-C$_{12}$ alkyl), or
S(O)$_n$(C$_1$-C$_{12}$ alkyl);
R6 is H, substituted or unsubstituted C$_6$-C$_{20}$ aryl, substituted or unsubstituted C$_1$-C$_{20}$ heterocyclyl;
R7 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R7, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9);
R8 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R8, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, C$_6$-C$_{20}$ aryl, or C$_1$-C$_{20}$ heterocyclyl, (each of which that can be substituted, may optionally be substituted with R9);
R9 (each independently) is H, CN, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, substituted or unsubstituted C$_1$-C$_{20}$ heterocyclyl, S(O)$_n$C$_1$-C$_6$ alkyl, N(C$_1$-C$_6$alkyl)$_2$,
  wherein each said R9, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OC$_1$-C$_6$ alkyl, OC$_1$-C$_6$ haloalkyl, S(O)$_n$C$_1$-C$_6$ alkyl, S(O)$_n$OC$_1$-C$_6$ alkyl, C$_6$-C$_{20}$ aryl, or C$_1$-C$_{20}$ heterocyclyl;
X1 is (each independently) O or S;
X2 is (each independently) O, S, =NR9, or =NOR9; and n is (each independently) 0, 1, or 2.
In another embodiment R1 is H or a C$_1$-C$_6$ haloalkyl.
In another embodiment R2 is H or Cl.
In another embodiment R3 is H, an unsubstituted C$_1$-C$_6$ alkyl, an unsubstituted C$_6$-C$_{20}$ aryl, or R9S(O)$_n$R9.

In another embodiment R3 is H, an unsubstituted C$_1$-C$_6$ alkyl, phenyl, or a (C$_1$-C$_6$ alkyl)S(O)$_n$(C$_1$-C$_6$ alkyl).
In another embodiment R4 is O or S.
In another embodiment R5 is (C$_1$-C$_{12}$ alkyl)S(O)$_n$(C$_1$-C$_{12}$ alkyl).
In another embodiment R6 is H or phenyl.
In another embodiment R7 is H, F, Cl, unsubstituted C$_1$-C$_6$ alkyl, C1-C6 haloalkyl, or N(R9)$_2$.
In another embodiment R8 is H or Cl.
In another embodiment R10 is

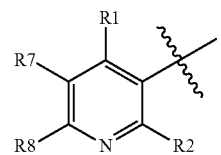

(a)

The molecules of Formula One will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

In the following schemes,

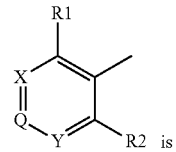

is

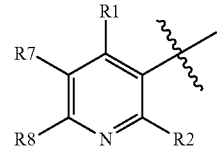

(a)

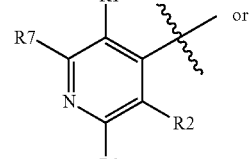

(b)

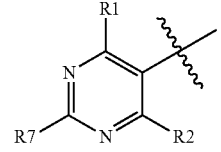

(c)

The following scheme illustrates approaches to generating 2-amino-1,3,4-thiadiazoles. In step a of Scheme I, treatment of the appropriate carboxylic acid of Formula IIa with a thiosemicarbazide of Formula III in an acid such as sulfuric acid or polyphosphoric acid afforded the 2-amino-1,3,4-thiadiazoles of Formula IV which was subsequently converted to the bromide via a diazonium intermediate in step b of Scheme I. The 2-amino-1,3,4-thiadiazole may also be converted to the chloride via a diazonium intermediate and copper in hydrochloric acid. These halothiadiazoles are reacted with the appropriate amines in step c to provide the 2-amino-1,3,4-thiadiazoles of Formula Va in Scheme I.

Scheme I

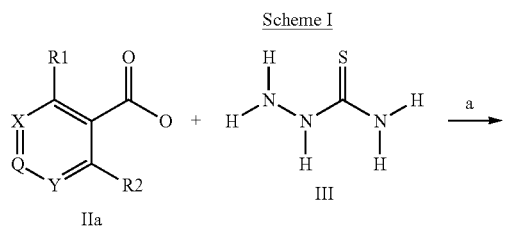

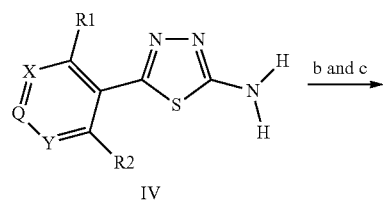

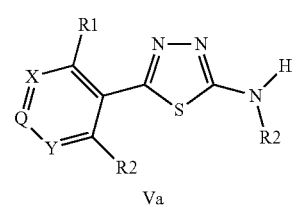

Yet another approach to 2-amino-1,3,4-thiadiazoles is illustrated in Scheme II. In step a of Scheme II treatment of the appropriate carboxaldehyde of Formula IIb can be condensed with a thiosemicarbazide of Formula VI in a polar aprotic solvent such as dimethylsulfoxide to give compounds of Formula VII. In step b compounds of Formula VII were subsequently cyclized using an oxidizing agent such as iron (III) chloride hexahydrate in a polar protic solvent such as ethanol to give the 2-amino-1,3,4-thiadiazole of Formula Vb in Scheme II.

Scheme II

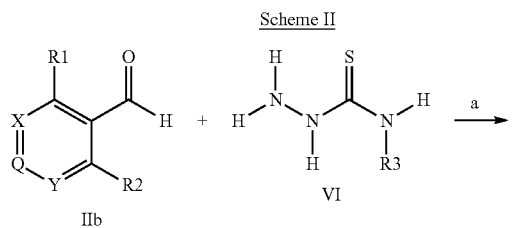

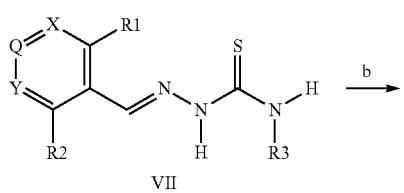

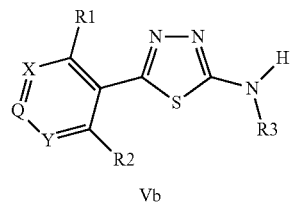

In step a of Scheme III, compounds of Formula Vc can be treated with an acid chloride of Formula VIII in the presence of a base such as N,N-dimethylaminopyridine in a polar aprotic solvent such as dichloroethane to yield compounds of Formula Ia. The acid chlorides used in the acylation reaction herein are either commercially available or can be synthesized by those skilled in the art.

Scheme III

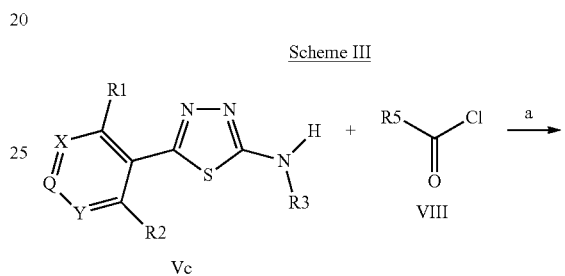

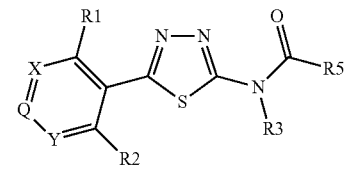

In step a and b of Scheme IV, ureas, thioureas, carbamates and thiocarbamates are prepared from the 2-amino-1,3,4-thiadiazoles of Formula Vd. Compounds of Formula Vd, wherein R1, R2 and R3 are as previously defined, are allowed to react with phosgene or thiophosgene to provide the intermediate carbamoyl chlorides or thiocarbamoyl chlorides, respectively. Alternatively, compounds of Formula Vd can be treated with a chloroformate, such as methyl chloroformate, and base, such as triethylamine, in an aprotic solvent, such as dichloromethane, to give a carbamate of Formula Ic as in step c. In step e of Scheme IV a compound of Formula Ib is treated with an amine to generate a urea or thiourea of Formula Id, wherein R4=O or S, respectively. Alkylation of the urea nitrogen of compounds of Formula Id, wherein R4=O with an alkyl halide such as iodomethane, in the presence of a base such as sodium hydride and in a polar aprotic solvent such as DMF yields the compounds of Formula If wherein R4=O as shown in step g of Scheme IV. In step d and f of Scheme IV the carbamoyl chloride is treated with an alcohol or thiol to give the carbamate of Formula Ic or a thiocarbamate of Formula Ie, respectively.

Scheme IV

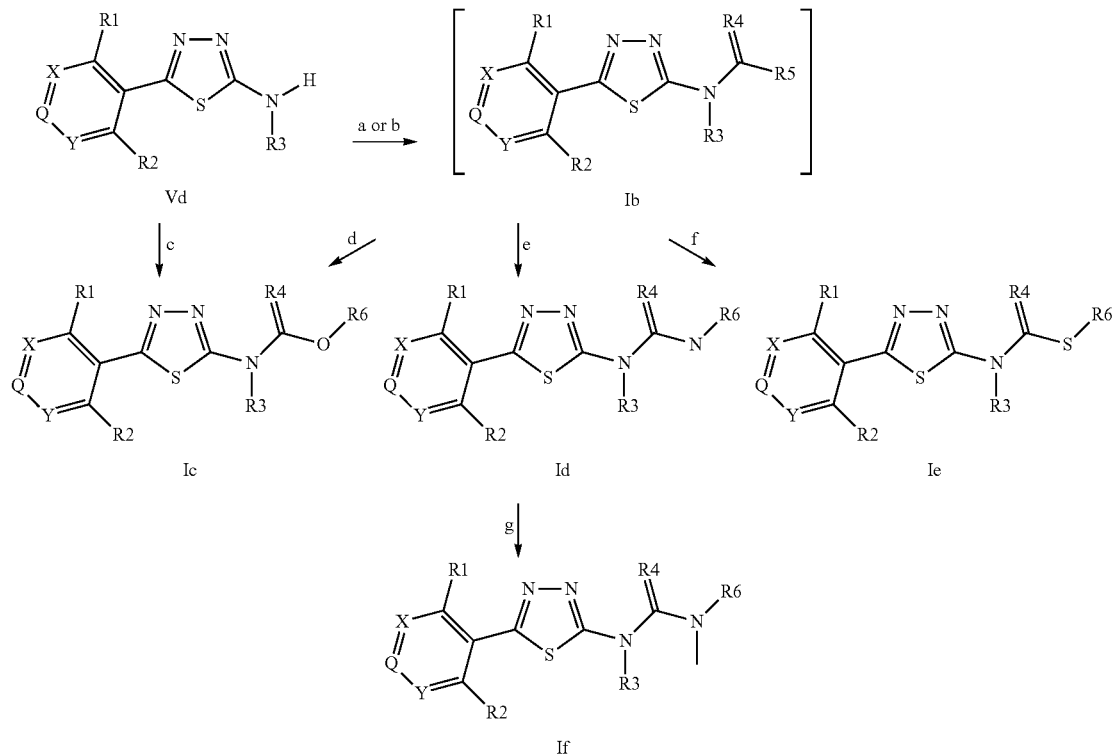

Oxidation of the sulfide to the sulfoxide or sulfone is accomplished as in Scheme V. The sulfide of Formula Ig, wherein X, R1, R2, and R3 are as previously defined, is treated with an oxidant such as sodium perborate tetrahydrate in a polar protic solvent such as glacial acetic acid to give the sulfoxide of Formula Ih as in step a of Scheme V. The sulfoxide of Formula Ih can be further oxidized to the sulfone of Formula II by sodium perborate tetrahydrate in a polar protic solvent such as glacial acetic acid as in step b of Scheme V. Alternatively, the sulfone of Formula II can be generated in a one-step procedure from the sulfide of Formula Ig by using the aforementioned conditions with ≥2 equivalents of the sodium perborate tetrahydrate as in step c of Scheme V.

Scheme V

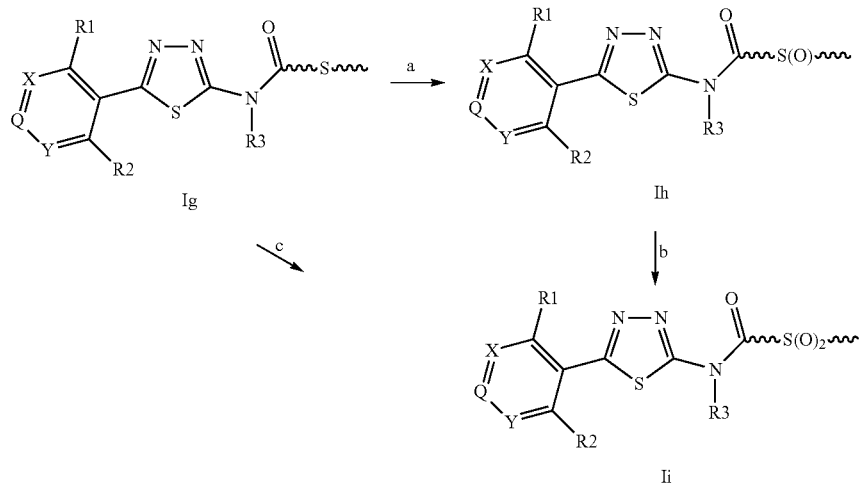

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1

Preparation of 5-pyridin-3-yl-[1,3,4]thiadiazol-2-ylamine

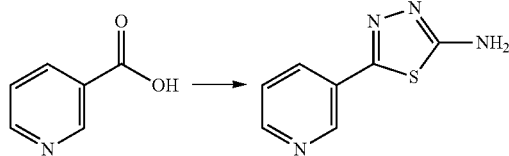 [SMILES: O=C(O)c1cccnc1 ; Nc1nnc(-c2cccnc2)s1]

5-pyridin-3-yl-[1,3,4]thiadiazol-2-ylamine was prepared as described by Turner et al. *J. Med. Chem.* 1988, 31, 898. Nicotinic acid (30 g, 0.24 mol) was added in portions to polyphosphoric acid (60 mL) under mechanical stirring. After stirring for 5 minutes, thiosemicarbazide (22.2 g, 0.24 mol) was added in portions. The reaction mixture was heated to 90° C. for 6 hours, cooled to room temperature over 14 hours, and re-heated to 40° C. to melt the solid yellow cake. Water was added (50 mL) dropwise via Pasteur pipette while stirring. The solution was cooled to 0° C., NH$_4$OH (29% solution, approx 250 mL) was added dropwise over 2.5 hours to bring the pH to 14. The solids were collected by filtration, washed with water (150 mL) and dried in vacuo at 65° C. for 16 hours to afford the title compound as a beige-colored solid (21.7 g, 50%): mp 201-211° C.; IR (KBr thin film) 1508 cm$^{-1}$; $^1$H NMR (300 MHz, DMSO-d$_6$) δ 8.95 (d, J=2.1 Hz, 1H), 8.62 (dd, J=4.5, 0.9 Hz, 1H), 8.14 (dt, J=8.4, 1.5 Hz, 1H), 7.51 (dd, J=8.1, 1.5 Hz, 1H); ESIMS m/z 179 ([M+H]$^+$).

Example 2

Preparation of 2-amino-5-(3-pyridyl)-1,3,4-thiadiazole

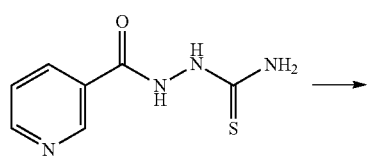

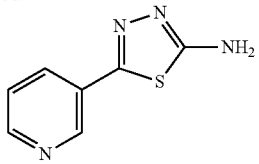

A mixture of the thiosemicarbazide (1.01 g, 4.34 mmol) in 5 mL of concentrated sulfuric acid was heated to 100° C. for 3 h. The reaction mixture was cooled to 23° C. and a 50% aqueous solution of sodium hydroxide was added until pH 9. The solid was collected, washed with water, and air dried to give 620 mg of 2-amino-5-(3-pyridyl)-1,3,4-thiadiazole. The filtrate was extracted with ethyl acetate. The ethyl acetate extracts were combined, dried over MgSO$_4$, and concentrated to dryness to give 0.120 g of 2-amino-5-(3-pyridyl)-1,3,4-thiadiazole. The lots were combined to give (0.738 g, 95%) of 2-amino-5-(3-pyridyl)-1,3,4-thiadiazole: $^1$H NMR (300 MHz, DMSO-d$_6$) δ 8.9 (d, 1H), 8.6 (dd, 1H), 8.1 (td, 1H), 7.57 (s, 2H), 7.5 (m, 1H).

Example 3

Preparation of N-Phenyl-5-(pyridin-3-yl)-1,3,4-thiadiazol-2-amine

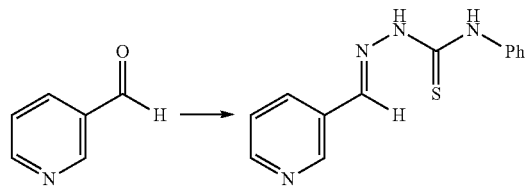 [SMILES: O=Cc1cccnc1 ; S=C(N/N=C/c1cccnc1)Nc1ccccc1]

Preparation of (E)-4-Phenyl-1-(pyridin-3-ylmethylene)-thiosemicarbazide

4-Phenylthiosemicarbazide (890 mg, 5.3 mmol, 1.0 equiv) was added to a stirred solution of nicotinaldehyde (500 μL, 5.3 mmol, 1.0 equiv) in methanol (2.5 mL) at 23° C. The resulting pale yellow solution was heated to 65° C. and stirred for 3 h. The cooled reaction mixture was concentrated under vacuum. The residue was rinsed with cold ethyl acetate and vacuum-filtered to afford the title compound as off-white crystals (1.3 g, 93%): mp 208-210° C.; IR (KBr thin film) 3442 (w), 3298 (m), 3125 (w), 2940 (w), 2791 (w), 1594 (s), 1532 (s) cm$^{-1}$; $^1$H NMR (300 MHz, DMSO-d$_6$) δ 11.98 (s, 1H), 10.22 (s, 1H), 9.03 (d, J=2 Hz, 1H), 8.59 (dd, J=5, 2 Hz, 1H), 8.38 (dt, J=8, 2 Hz, 1H), 8.18 (s, 1H), 7.55 (m, 2H), 7.45 (dd, J=8, 5 Hz, 1H), 7.21 (m, 1H); ESIMS m/z 257 ([M+H]$^+$).

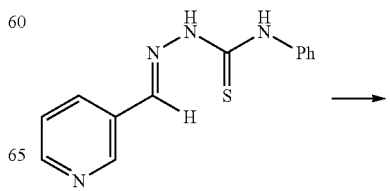

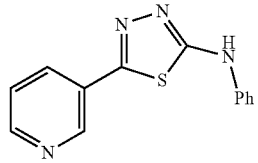

Preparation of N-Phenyl-5-(pyridin-3-yl)-1,3,4-thiadiazol-2-amine

Powdered iron(III) chloride hexahydrate (5.1 g, 19 mmol, 4.0 equiv) was added to a stirred suspension of (E)-4-phenyl-1-(pyridin-3-ylmethylene)thiosemicarbazide (1.2 g, 4.7 mmol, 1.0 equiv) in absolute ethanol (47 mL) at 23° C. The resulting dark brown suspension was heated to 95° C. and stirred for 2 h. The cooled reaction mixture was concentrated by rotary evaporation. The residue was diluted with a 1M solution of sodium hydroxide (200 mL) and extracted with dichloromethane (8×75 mL). The combined organic layers were dried ($Na_2SO_4$), gravity-filtered, and concentrated by rotary evaporation to afford the title compound as a tan solid (300 mg, 25%): mp 252-255° C.; IR (KBr thin film) 3460 (w), 3260 (w), 3198 (w), 2921 (w), 2851 (w), 2788 (w), 1620 (m), 1566 (m), 1501 (s) $cm^{-1}$; $^1$H NMR (300 MHz, DMSO-$d_6$) δ 10.65 (s, 1H), 9.05 (d, J=2 Hz, 1H), 8.67 (dd, J=5, 2 Hz, 1H), 7.66 (m, 2H), 7.56 (dd, J=8, 5 Hz, 1H), 7.38 (m, 2H), 7.05 (m, 1H); ESIMS m/z 255 ([M+H]$^+$).

Precursors N-methyl-5-[4-(trifluoromethyl)pyridin-3-yl]-1,3,4-thiadiazol-2-amine, N-methyl-5-[4-(trifluoromethyl)pyridin-3-yl]-1,3,4-thiadiazol-2-amine, N-methyl-5-pyrimidin-5-yl-1,3,4-thiadiazol-2-amine, 5-(6-chloropyridin-3-yl)-N-methyl-1,3,4-thiadiazol-2-amine, 5-(5-fluoropyridin-3-yl)-N-methyl-1,3,4-thiadiazol-2-amine, 5-(5-chloropyridin-3-yl)-N-methyl-1,3,4-thiadiazol-2-amine, N-methyl-5-(2-methylpyrimidin-5-yl)-1,3,4-thiadiazol-2-amine, N,N-dimethyl-5-[5-(methylamino)-1,3,4-thiadiazol-2-yl]pyrimidin-2-amine, N-methyl-5-[5-(trifluoromethyl)pyridin-3-yl]-1,3,4-thiadiazol-2-amine, N-methyl-5-pyridin-4-yl-1,3,4-thiadiazol-2-amine, and N-methyl-5-(5-methylpyridin-3-yl)-1,3,4-thiadiazol-2-amine were prepared as described in Example 3.

Example 4

Preparation of 3-(5-bromo-[1,3,4]thiadiazol-2-yl)pyridinium hydrobromide

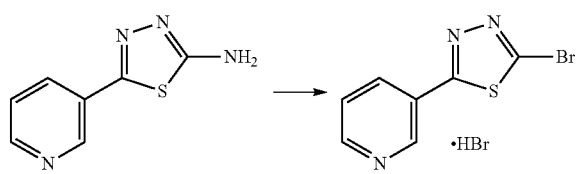 [SMILES: Nc1nnc(-c2cccnc2)s1 ; Brc1nnc(-c2cccnc2)s1 ; Br]

To a solution of aqueous hydrobromic acid (48%, 17 mL) at 5° C. in an ice bath was added 5-pyridin-3-yl-[1,3,4]thiadiazol-2-ylamine (6 g, 33 mmol) followed by bromine (12.8 mL, 0.24 mol) at a rate such that the reaction mixture was kept at a temperature below 11° C. A solution of sodium nitrite (6 g, 85 mmol) in water (8.5 mL) was added at a rate such that the reaction mixture maintained a temperature of around 5° C.

The reaction mixture was kept at 2° C. for 2 hours, and then made basic to pH 8.9 using dilute NaOH at a rate needed to maintain the temperature between 5° C. and 15° C. The resulting solids were collected by filtration, washed with ice-cold water (200 mL) until filtrate was acidic (pH 4), and dried in vacuo at 35° C. to afford the title compound as an orange powder (8.68 g, 80%): mp 124-129° C.; IR (KBr thin film) 1374, 1026 $cm^{-1}$; $^1$H NMR (300 MHz, DMSO-$d_6$) δ 9.17 (d, J=1.8 Hz, 1H), 8.80 (dd, J=4.5, 0.9 Hz, 1H), 8.42 (dt, J=8.4, 1.8 Hz, 1H), 7.67 (ddd, J=7.2, 4.8, 0.9 Hz, 1H); ESIMS m/z 244 (M+2).

Example 5

Preparation of 2-chloro-5-(3-pyridyl)-[1,3,4]-thiadiazole

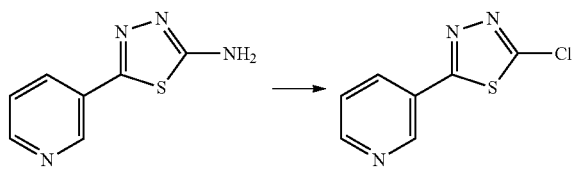 [SMILES: Nc1nnc(-c2cccnc2)s1 ; Clc1nnc(-c2cccnc2)s1]

To a mixture of 5-pyridin-3-yl-[1,3,4]thiadiazol-2-ylamine (5.5 g, 30.9 mmol) and copper powder (0.335 g, 5.27 mmol), in a mixture of glacial acetic acid (93 mL) and concentrated hydrochloric acid (19 mL) at 0° C., was added dropwise a solution of sodium nitrite (10.67 g, 154.6 mmol) dissolved in water (13 mL). The reaction mixture was then allowed to warm to 23° C. overnight. The reaction mixture was diluted with 300 g of ice, resulting in an emulsion, and extracted with dichloromethane (3×200 mL). The emulsion was then passed through a medium porosity scintered glass funnel containing celite. The cake was stirred and washed well with chloroform. The filtrate was combined with the organic extracts. The organic phase was dried over $MgSO_4$ and concentrated to dryness to give the title compound as a yellow solid (4.42 g, 72%): $^1$H NMR (300 MHz, CDCl$_3$) δ 9.08 (br s, 1H), 8.78 (br s, 1H), 8.29 (dt, J=8, 2 Hz, 1H), 7.49 (dd, J=8, 5 Hz, 1H).

Example 6

Preparation of N-ethyl-5-pyridin-3-yl-1,3,4-thiadiazol-2-amine

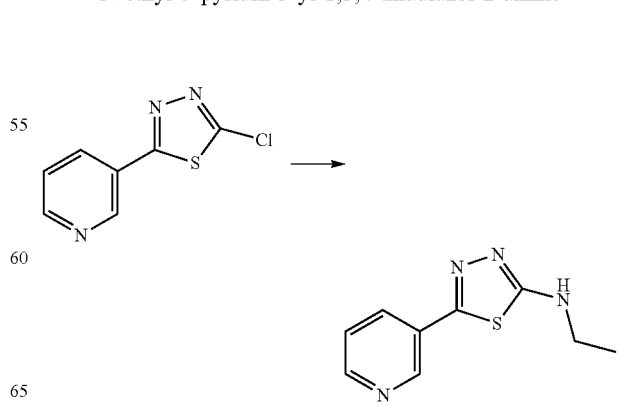

N-ethyl-5-pyridin-3-yl-1,3,4-thiadiazol-2-amine can be prepared from 2-chloro-5-(3-pyridyl)-[1,3,4]-thiadiazole as described by Chapleo et al. in *J. Med. Chem,* 1987, 30(5), 951.

Example 6A

Preparation of N-(cyclopropylmethyl)-5-(3-pyridyl)-1,3,4-thiadiazol-2-amine

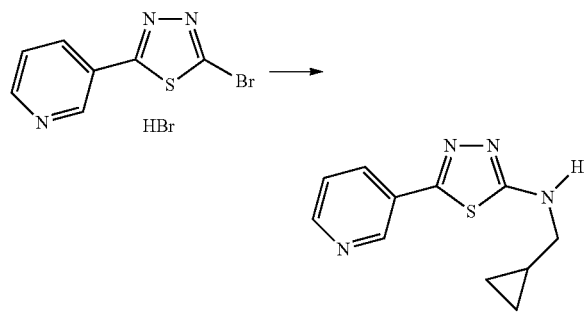

A suspension of cyclopropylmethanamine (0.528 g, 0.743 mmol), 2-bromo-5-(3-pyridyl)-1,3,4-thiadiazole hydrobromide (0.2 g, 0.619 mmol) and triethylamine (0.3 ml, 2.16 mmol) in ethanol (20 mL) was heated to 125° C. for 42 minutes in a microwave reaction vessel, cooled to room temperature, concentrated under reduced pressure and resuspended in 2:1 saturated aqueous sodium bicarbonate:ethyl acetate (100 mL). The suspension was shaken vigorously and the organic extract collected and washed with water (50 mL) and brine (30 mL) before drying over magnesium sulfate. The solution was concentrated under reduced pressure and purified by silica column chromatography, eluting with a gradient of methanol in ethyl acetate. The slower eluting fraction was concentrated under reduced pressure to afford the title compound as a yellow solid (38 mg, 26%): mp 162-165° C.; IR (ATR) 1573 (s), 1549 (s), 1464 (m), 1063 (m) cm$^{-1}$; $^1$H NMR (400 MHz, CDCl$_3$) δ 8.97 (d, J=1.6 Hz, 1H), 8.63 (dd, J=4.8, 1.6 Hz, 1H), 8.18 (ddd, J=8.0, 2.2, 1.7 Hz, 1H), 7.38 (ddd, J=8.0, 4.8, 0.7 Hz, 1H), 5.68 (s, 1H), 3.29 (d, J=7.1 Hz, 2H), 1.26-1.09 (m, 1H), 0.72-0.53 (m, 2H), 0.42-0.25 (m, 2H); $^{13}$C NMR (101 MHz, CDCl$_3$) δ 170.01, 154.19, 150.61, 147.94, 133.64, 127.47, 123.76, 52.20, 10.76, 3.73; ESIMS m/z 231.8 ([M−H]$^-$).

Example 7

Preparation of N-2-Dimethyl-3-(methylthio)-N-(5-(pyridin-3-yl)-1,3,4-thiadiazol-2-yl)propanamide (Compound 28)

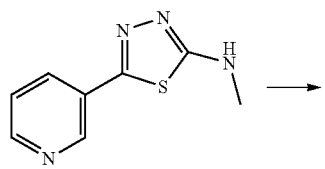

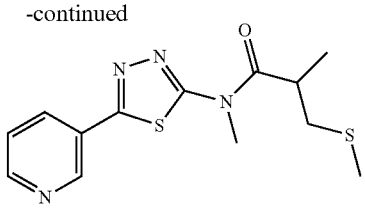

Oxalyl chloride (980 μL, 11 mmol, 1.5 equiv) and N,N-dimethylformamide (29 μL, 0.37 mmol, 0.05 equiv) were sequentially added to a stirred suspension of 2-methyl-3-(methylthio)propanoic acid (1.0 g, 7.5 mmol, 1.0 equiv) in dichloromethane (13 mL) at 23° C. The resulting bubbling yellow solution was stirred at 23° C. for 2 h. The reaction mixture was concentrated by rotary evaporation. A portion of the resulting product, 2-methyl-3-(methylthio)propanoyl chloride (120 mg, 0.79 mmol, 1.5 equiv), was added to a stirred suspension of N-methyl-5-(pyridin-3-yl)-1,3,4-thiadiazol-2-amine (100 mg, 0.52 mmol, 1.0 equiv) and 4-dimethylaminopyridine (130 mg, 1.1 mmol, 2.0 equiv) in 1,2-dichloroethane (3.0 mL) at 23° C. The resulting yellow solution was heated to 75° C. for 3 h. The cooled reaction mixture was diluted with a saturated solution of sodium bicarbonate (50 mL) and extracted with ethyl acetate (3×40 mL). The combined organic layers were dried (MgSO$_4$), gravity filtered, and concentrated by rotary evaporation. The residue was purified by silica gel column chromatography (ethyl acetate) to afford a brown semi-solid (70 mg, 44%): IR (KBr thin film) 2975 (w), 2917 (w), 1667 (m) cm$^{-1}$; $^1$H NMR (300 MHz, CDCl$_3$) δ 9.15 (d, J=2 Hz, 1H), 8.69 (dd, J=5, 2 Hz, 1H), 8.28 (dt, J=8, 2 Hz, 1H), 7.42 (dd, J=8, 5 Hz, 1H), 3.94 (s, 3H), 3.33 (m, 1H), 3.01 (dd, J=13, 8 Hz, 1H), 2.69 (dd, J=13, 6 Hz, 1H), 2.15 (s, 3H), 1.37 (d, J=7 Hz, 3H); ESIMS m/z 309 ([M+H]$^+$).

Example 8

Preparation of N-2,2-trimethyl-3-(methylthio)-N-(5-(pyridin-3-yl)-1,3,4-thiadiazol-2-yl)propanamide (Compound 24)

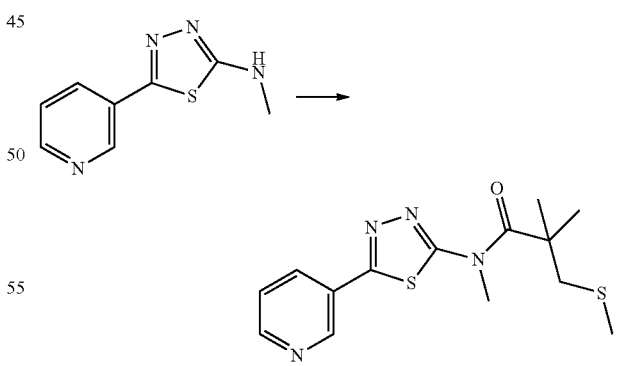

Oxalyl chloride (500 μL, 5.8 mmol, 1.5 equiv) and N,N-dimethylformamide (15 μL, 0.19 mmol, 0.05 equiv) were sequentially added to a stirred suspension of 2,2-dimethyl-3-(methylthio)propanoic acid (570 mg, 3.8 mmol, 1.0 equiv) in dichloromethane (13 mL) at 23° C. The resulting bubbling yellow solution was stirred at 23° C. for 1.5 h. The reaction mixture was concentrated by rotary evaporation. A portion of the resulting product, 2,2-dimethyl-3-(methylthio)propanoyl chloride (110 mg, 0.66 mmol, 1.3 equiv), was added to a stirred suspension of N-methyl-5-(pyridin-3-yl)-1,3,4-thiadiazol-2-amine (100 mg, 0.52 mmol, 1.0 equiv) and 4-dimethylaminopyridine (95 mg, 0.78 mmol, 1.5 equiv) in 1,2-dichloroethane (3.0 mL) at 23° C. The resulting yellow solution was heated to 75° C. for 17 h. The cooled reaction mixture was diluted with a saturated solution of sodium bicarbonate (40 mL) and extracted with ethyl acetate (3×30 mL). The combined organic layers were dried (MgSO$_4$), gravity-filtered, and concentrated by rotary evaporation. The residue was purified by silica gel column chromatography (ethyl acetate) to afford pale yellow crystals (140 mg, 82%): mp 89-91° C.; $^1$H NMR (300 MHz, CDCl$_3$) δ 9.13 (d, J=2 Hz, 1H), 8.66 (dd, J=5, 2 Hz, 1H), 8.25 (dt, J=8, 2 Hz, 1H), 7.40 (dd, J=8, 5 Hz, 1H), 3.95 (s, 3H), 2.95 (s, 2H), 2.15 (s, 3H), 1.54 (s, 6H); ESIMS m/z 323 ([M+H]$^+$).

Compounds 1, 2, 3, 4, 5, 6, 7, 8, 9, 10, 11, 12, 13, 17, 19, 24, 29, 30, 31, 34, 35, 44, 47, 49, 53, 57, 58, 60, 62, 64, 66, 67, 70, 71, 72, 73, 74, 75, 81, 84, 88, 90, 91, 92, 93, 94, and 96 were prepared as described in Example 8.

Example 9

Preparation of methyl 4-(methyl-(5-(pyridin-3-yl)-1,3,4-thiadiazol-2-yl)amino)-4-oxobutanoate (Compound 56)

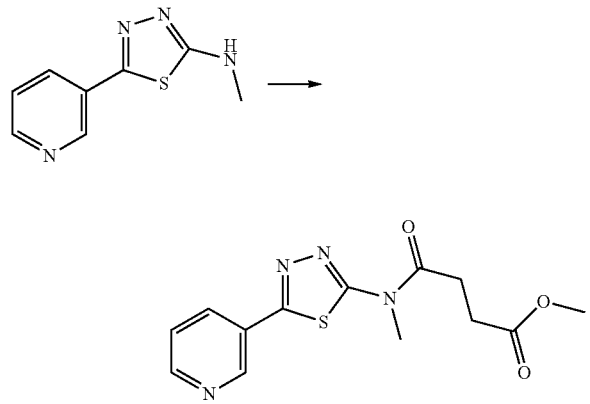 [SMILES: CNc1nnc(-c2cccnc2)s1 ; COC(=O)CCC(=O)N(C)c1nnc(-c2cccnc2)s1]

4-methoxy-4-oxobutanoic acid (69 mg, 0.52 mmol, 2.0 equiv) and 4-dimethylamino-pyridine (64 mg, 0.52 mmol, 2.0 equiv) were sequentially added to a stirred suspension of N-methyl-5-(pyridin-3-yl)-1,3,4-thiadiazol-2-amine (50 mg, 0.26 mmol, 1.0 equiv) and 1-ethyl-3-(3-dimethylaminopropyl)-carbodiimide hydrochloride (200 mg, 1.0 mmol, 4.0 equiv) in 1,2-dichloroethane (2.6 mL) at 23° C. The resulting orange solution was stirred at 23° C. for 18 h. The reaction mixture was directly subjected to silica gel column chromatography (ethyl acetate) to afford an off-white powder (59 mg, 74% yield): mp 152-154° C.; IR (KBr thin film) 3032 (w), 2951 (w), 1737 (s), 1667 (s) cm$^{-1}$; $^1$H NMR (300 MHz, CDCl$_3$) δ 9.14 (dd, 1H, J=2, 1 Hz), 8.69 (dd, 1H, J=5, 2 Hz), 8.28 (m, 1H), 7.42 (ddd, 1H, J=8, 5, 1 Hz), 3.90 (s, 3H), 3.74 (s, 3H), 3.03 (dd, 2H, J=8, 6 Hz), 2.83 (dd, 2H, J=8, 6 Hz); ESIMS m/z 307 ([M+H]$^+$).

Compounds 38, 59, 61, 63, 65, 68, 69, 97 and 98 were prepared as described in Example 9.

Example 10

Preparation of N-methyl-3-(methylsulfinyl)-N-(5-(pyridin-3-yl)-1,3,4-thiadiazol-2-yl)propanamide (Compound 18)

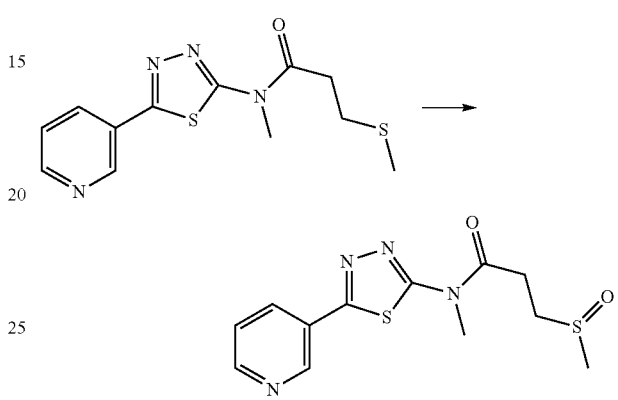

Sodium perborate tetrahydrate (52 mg, 0.34 mmol, 1.0 equiv) was added to a stirred solution of N-methyl-3-(methylthio)-N-(5-(pyridin-3-yl)-1,3,4-thiadiazol-2-yl)propanamide (100 mg, 0.34 mmol, 1.0 equiv) in glacial acetic acid (1.8 mL) at 23° C. The resulting suspension was stirred at 23° C. for 3 h. The reaction mixture was diluted with a saturated solution of sodium bicarbonate (50 mL) and extracted with dichloromethane (5×20 mL). The combined organic layers were dried (Na$_2$SO$_4$), gravity-filtered, and concentrated by rotary evaporation. The residue was rinsed with cold ethyl acetate and vacuum-filtered to afford the title compound as an off-white powder (82 mg, 78% yield): mp 138-140° C.; $^1$H NMR (300 MHz, DMSO-d$_6$) δ 9.12 (d, J=2 Hz, 1H), 8.71 (dd, J=5, 2 Hz, 1H), 8.34 (m, 1H), 7.56 (dd, J=8, 5 Hz, 1H), 3.80 (s, 3H), 2.90-3.30 (m, 3H), 2.62 (s, 3H); ESIMS m/z 311 ([M+H]$^+$).

Compounds 32, 45, 51, and 77 were prepared as described in Example 10.

Example 11

Preparation of N-methyl-3-(methylsulfonyl)-N-(5-(pyridin-3-yl)-1,3,4-thiadiazol-2-yl)propanamide (Compound 20)

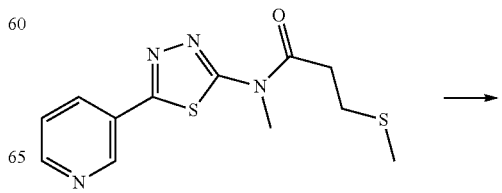

-continued

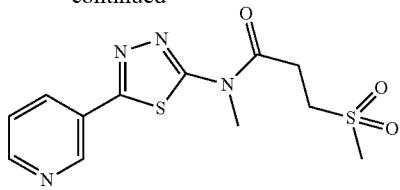

Sodium perborate tetrahydrate (130 mg, 0.84 mmol, 2.4 equiv) was added to a stirred solution of N-methyl-3-(methylthio)-N-(5-(pyridin-3-yl)-1,3,4-thiadiazol-2-yl)propanamide (100 mg, 0.34 mmol, 1.0 equiv) in glacial acetic acid (1.8 mL) at 23° C. The resulting yellow suspension was heated to 60° C. for 15 h. The cooled reaction mixture was diluted with a saturated solution of sodium bicarbonate (50 mL) and extracted with dichloromethane (3×30 mL). The combined organic layers were dried (sodium sulfate), gravity filtered, and concentrated by rotary evaporation. The residue was rinsed with cold ethyl acetate and vacuum-filtered to afford the title compound as an off-white powder (90 mg, 82% yield): mp 199-201° C.; $^1$H NMR (300 MHz, DMSO-$d_6$) δ 9.15 (d, J=2 Hz, 1H), 8.73 (dd, J=6, 2 Hz, 1H), 8.32 (dt, J=8, 2 Hz, 1H), 7.46 (dd, J=8, 5 Hz, 1H), 3.94 (s, 3H), 3.59 (t, J=7 Hz, 2H), 3.33 (t, J=7 Hz, 2H), 3.09 (s, 3H); ESIMS m/z 327 ([M+H]$^+$).

Compounds 33, 36, 37, 40, 43, 46, 52, 76 were prepared as described in Example 11.

Example 12

Preparation of 2-(Methylthio)ethyl methyl(5-(pyridin-3-yl)-1,3,4-thiadiazol-2-yl)carbamate (Compound 50)

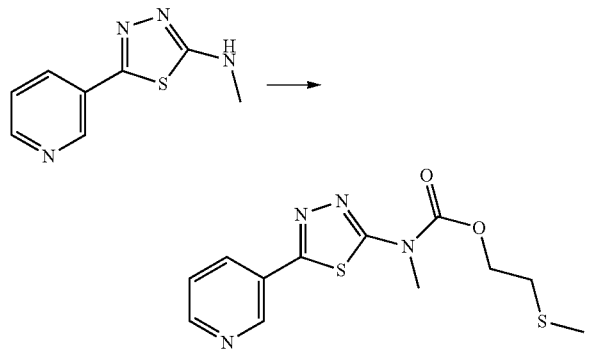

2-Methylthioethanol (100 µL, 1.2 mmol, 1.5 equiv) was added to a stirred 20% solution of phosgene in toluene (1.2 mL, 2.3 mmol, 3.0 equiv) at 0° C. The resulting colorless solution was allowed to warm to 23° C. and stirred for 1.5 h. The reaction mixture was concentrated by rotary evaporation. The residue was added to a stirred suspension of N-methyl-5-(pyridin-3-yl)-1,3,4-thiadiazol-2-amine (150 mg, 0.78 mmol, 1.0 equiv) and 4-dimethylaminopyridine (190 mg, 1.6 mmol, 2.0 equiv) in 1,2-dichloroethane (7.8 mL) at 23° C. The resulting yellow solution was heated to 75° C. for 18 h. The cooled reaction mixture was diluted with a saturated solution of sodium bicarbonate (50 mL) and extracted with ethyl acetate (3×40 mL). The combined organic layers were dried (MgSO$_4$), gravity filtered, and concentrated by rotary evaporation. The residue was purified by silica gel column chromatography (ethyl acetate) to afford the title compound as a white powder (190 mg, 79%): mp 126-128° C.; IR (KBr thin film) 3044 (w), 2958 (w), 2910 (w), 1700 (s), 1572 (w) cm$^{-1}$; $^1$H NMR (300 MHz, CDCl$_3$) δ 9.12 (br s, 1H), 8.70 (d, J=5 Hz, 1H), 8.27 (dt, J=8, 2 Hz, 1H), 7.42 (dd, J=8, 5 Hz, 1H), 4.51 (t, J=7 Hz, 2H), 3.75 (s, 3H), 2.87 (t, J=7 Hz, 2H), 2.21 (s, 3H); ESIMS m/z 311 ([M+H]$^+$).

Compounds 14, 15, and 16 were prepared as described in Example 12.

Example 13

Preparation of [5-(5-fluoropyridin-3-yl)-[1,3,4]thiadiazol-2-yl]-methylcarbamic acid 2-methylsulfanylethyl ester (Compound 78)

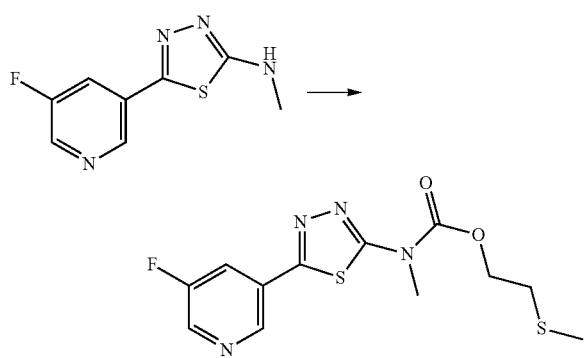

A solution of phosgene (20%, 0.39 mL, 0.8 mmol) in toluene was pipetted at a dropwise rate into a suspension of methyl-[5-(5-fluoropyridin-3-yl)-[1,3,4]thiadiazol-2-yl]-amine (0.15 g, 0.7 mmol) in dichloroethane (10 mL) at 1° C., stirred for 5 minutes and treated with a solution of 4-N,N-dimethylaminopyridine (0.192 g, 1.6 mmol) in dichloroethane (3 mL). The ice bath was removed after 30 minutes. The reaction mixture was stirred at 23° C. for 90 minutes, refluxed under nitrogen for 14 hours, cooled to 0° C. and reacted with 2-methylthio ethanol (0.033 g, 0.35 mmol). The ice bath was removed after 10 minutes. The reaction mixture was stirred at 23° C. for 1 hour, refluxed for 1 hour, cooled, and diluted with dichloroethane (30 mL). The reaction mixture was washed with dilute hydrochloric acid (0.1 N, 2×20 mL), saturated aqueous NaHCO$_3$ (40 mL), and brine (30 mL), and then dried over MgSO$_4$ and chromatographed on silica to afford the title compound as a white solid (0.125 g, 53%): mp 104-106° C.; $^1$H NMR (400 MHz, CDCl$_3$) δ 8.90 (br t, 1H), 8.56 (d, J=2.8 Hz, 1H), 8.04 (ddd, J=9.1, 2.5, 1.0 Hz, 1H), 4.52 (t, J=6.8 Hz, 2H), 3.75 (s, 3H), 2.87 (t, J=6.8 Hz, 2H), 2.21 (s, 3H); ESIMS m/z 329 ([M+H]$^+$).

Example 14

Preparation of methylthiomethyl methyl(5-(pyridin-3-yl)-1,3,4-thiadiazol-2-yl)carbamate (Compound 54)

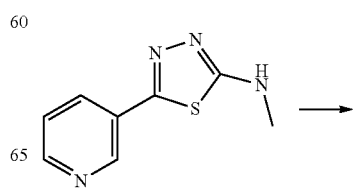

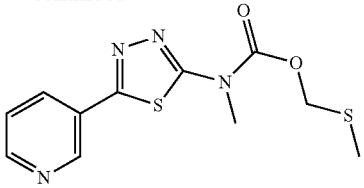

A 37% aqueous solution of formaldehyde (400 µL, 4.8 mmol, 6.0 equiv) was added to a stirred solution of sodium methanethiolate (170 mg, 2.4 mmol, 3.0 equiv) in water (2.0 mL) at 23° C. The resulting colorless solution was stirred at 23° C. for 2 h. The reaction mixture was extracted with diethyl ether (3×2 mL). The combined organic layers were dried (magnesium sulfate) and gravity-filtered. Pyridine (320 µL, 3.9 mmol, 5.0 equiv) was added and the resulting solution was added to a stirred 20% solution of phosgene in toluene (4.0 mL, 7.8 mmol, 10 equiv) at 0° C. The resulting white mixture was allowed to warm to 23° C. and stirred for 2 h. The reaction mixture was gravity filtered and concentrated under vacuum. The residue was added to a stirred suspension of N-methyl-5-(pyridin-3-yl)-1,3,4-thiadiazol-2-amine (150 mg, 0.78 mmol, 1.0 equiv) and 4-dimethylaminopyridine (290 mg, 2.4 mmol, 3.0 equiv) in 1,2-dichloroethane (7.8 mL) at 23° C. The resulting yellow solution was heated to 75° C. for 18 h. The cooled reaction mixture was diluted with a saturated solution of sodium bicarbonate (50 mL) and extracted with ethyl acetate (3×40 mL). The combined organic layers were dried (MgSO$_4$), gravity-filtered, and concentrated by rotary evaporation. The residue was purified by silica gel column chromatography (ethyl acetate) to afford the title compound as a yellow film (27 mg, 12%): IR (KBr thin film) 2919 (w), 1647 (s), 1570 (w) cm$^{-1}$; $^1$H NMR (300 MHz, CDCl$_3$) δ 8.89 (br s, 1H), 8.64 (br s, 1H), 7.97 (dt, J=8, 2 Hz, 1H), 7.37 (dd, J=8, 5 Hz, 1H), 5.12 (s, 2H), 3.14 (s, 3H), 2.32 (s, 3H).

Example 15

Preparation of S-methyl methyl(5-(pyridin-3-yl)-1,3,4-thiadiazol-2-yl)carbamothioate (Compound 55)

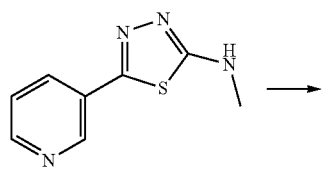

4-Dimethylaminopyridine (81 mg, 0.66 mmol, 1.5 equiv) and methyl chlorothiolformate (50 µL, 0.57 mmol, 1.3 equiv) were sequentially added to a stirred suspension of N-methyl-5-(pyridin-3-yl)-1,3,4-thiadiazol-2-amine (85 mg, 0.44 mmol, 1.0 equiv) in dichloroethane (3.4 mL) at 23° C. The resulting solution was heated to 75° C. and stirred for 72 h. The cooled reaction mixture was directly subjected to silica gel column chromatography (55% ethyl acetate in hexane spiked with 5% triethylamine) to afford the title compound as an off-white powder (100 mg, 83%): mp 192-194° C.; IR (KBr thin film) 2931 (w), 1727 (w), 1634 (s), 1570 (w) cm$^{-1}$; $^1$H NMR (300 MHz, CDCl$_3$) δ 9.13 (d, J=2 Hz, 1H), 8.70 (dd, J=5, 2 Hz, 1H), 8.28 (dt, J=8, 2 Hz, 1H), 7.43 (dd, J=8, 5 Hz, 1H), 3.86 (s, 3H), 2.53 (s, 3H); ESIMS m/z 267 ([M+H]$^+$).

Compound 87 was prepared as described in Example 15.

Example 16

Preparation of [5-(5-fluoro-pyridin-3-yl)-[1,3,4]thiadiazol-2-yl]-methyl-thiocarbamic acid 2-methylsulfanyl-ethyl ester—(Compound 85)

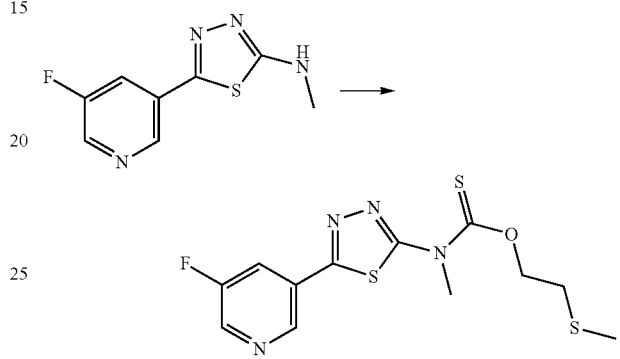

A solution of thiophosgene (0.086 g, 0.7 mmol) in dichloroethane (1 mL) was pipetted at a dropwise rate into an ice-cold suspension of methyl-[5-(5-fluoropyridin-3-yl)-[1,3,4]thiadiazol-2-yl]-amine (0.15 g, 0.7 mmol) in dichloroethane (1 mL), stirred for 10 minutes and treated with a solution of 4-N,N-dimethylaminopyridine (0.105 g, 0.8 mmol) in dichloroethane (1 mL). The ice bath was removed after 10 minutes and, after stirring at room temperature for 30 minutes, the reaction was refluxed under nitrogen for 2 hours. The reaction mixture was then cooled to 0° C. and reacted with a solution of 2-methylthio ethanol (0.072 g, 0.8 mmol) in dichloroethane (1 mL). After stirring the reaction mixture for 10 minutes, a solution of N,N-dimethylaminopyridine (0.105 g, 0.8 mmol) in dichloroethane (1 mL) was added via pipette. The ice bath was removed after 10 minutes. The reaction mixture was stirred at room temperature for 15 minutes, refluxed under nitrogen for 14 hours, cooled, concentrated under reduced pressure and purified using reversed phase chromatography to afford the title compound as a yellow solid (0.043 g, 17%): mp 150-152° C.; $^1$H NMR (400 MHz, CDCl$_3$,) δ 8.91 (s, 1H), 8.57 (d, J=2.5 Hz, 1H), 8.05 (ddd, J=8.8, 2.8, 1.8 Hz, 1H), 3.86 (s, 3H), 3.33-3.30 (m, 2H), 2.84-2.80 (m, 2H), 2.22 (s, 3H); ESIMS m/z 345 ([M+H]$^+$).

Example 17

Preparation of [5-(5-fluoro-pyridin-3-yl)-[1,3,4]thiadiazol-2-yl]-methyl-thiocarbamic acid ethyl ester—(Compound 80)

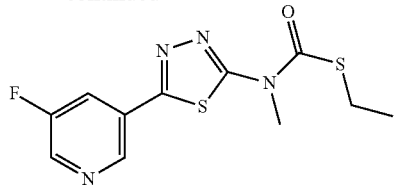

A 20% solution of phosgene in toluene (0.26 mL, 0.5 mmol) was pipetted at a dropwise rate into an ice-cold suspension of methyl-[5-(5-fluoropyridin-3-yl)-[1,3,4]thiadiazol-2-yl]-amine (0.1 g, 0.5 mmol) in dichloroethane (3 mL), stirred for 10 minutes, and treated with a solution of N,N-dimethylaminopyridine (0.128 g, 1 mmol) in dichloroethane (2 mL). The ice bath was removed after 10 minutes and, after stirring at room temperature for 30 minutes, the reaction was refluxed under nitrogen for 2 hours, cooled to 1° C., and reacted with neat ethanethiol (0.031 g, 0.5 mmol). The ice bath was removed after 10 minutes and, after stirring at room temperature for 30 minutes, the reaction was refluxed under nitrogen for 9 hours, cooled to room temperature, and diluted with dichloroethane (40 mL). The reaction mixture was washed with dilute hydrochloric acid (0.1 N, 2×20 mL), saturated aqueous sodium bicarbonate (50 mL), brine (30 mL), dried over MgSO$_4$ and chromatographed on silica to give the title compound as a white solid (0.154 g, 100%): $^1$H NMR (CDCl$_3$, 400 MHz) δ 8.91 (s, 1H), 8.56 (d, J=2.8 Hz, 1H), 8.06 (ddd, J=8.8, 2.8, 1.8 Hz, 1H), 3.84 (s, 3H), 3.10 (q, J=7.4 Hz, 2H), 1.41 (t, J=7.4 Hz, 2H); ESIMS m/z 299 ([M+H]$^+$).

Example 18

Preparation of 1-[5-(5-fluoro-pyridin-3-yl)-[1,3,4]thiadiazol-2-yl]-1-methyl-3-(2-methylsulfanyl-ethyl)-thiourea—(Compound 86)

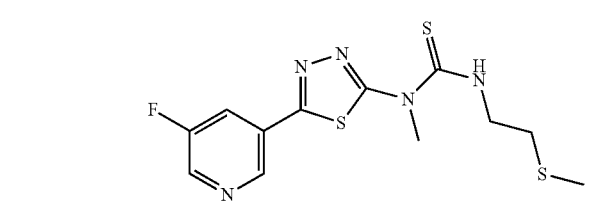

A solution of thiophosgene (0.13 mL, 1.7 mmol) in dichloroethane (1 mL) was pipetted at a dropwise rate into an ice-cold suspension of methyl-[5-(5-fluoropyridin-3-yl)-[1,3,4]thiadiazol-2-yl]-amine (0.319 g, 1.5 mmol) in dichloroethane (5 mL). The reaction mixture was stirred for 10 minutes and treated with a solution of 4-N,N-dimethylaminopyridine (0.222 g, 1.8 mmol) in dichloroethane (2 mL). The ice bath was removed after 15 minutes. The reaction mixture was stirred at room temperature for 20 minutes, refluxed under nitrogen for 4 hours, cooled to 0° C., and treated with a solution of 2-methylsulfanyl-ethylamine (0.145 g, 1.6 mmol) in dichloroethane (1 mL). The reaction mixture was stirred for 5 minutes before adding a solution of 4-N,N-dimethylaminopyridine (0.222 g, 1.8 mmol) in dichloroethane (2 mL), followed by removal of the ice bath after 15 minutes. The reaction mixture was stirred at room temperature for 20 minutes, refluxed under nitrogen for 14 hours, cooled, concentrated under reduced pressure, and purified by reversed phase high performance liquid chromatography to give the title compound as a brown glass (0.051 g, 10%): $^1$H NMR (400 MHz, DMSO-d$_6$) δ 9.22 (t, J=5.3 Hz, 1H), 8.98 (s, 1H), 8.72 (d, J=2.8 Hz, 1H), 8.26 (dt, J=9.4, 2.3 Hz, 1H). 3.88 (s, 3H), 3.83-3.78 (m, 2H), 2.77 (t, J=7.3 Hz, 2H), 2.14 (s, 3H); ESIMS m/z 344 ([M+H]$^+$).

Compound 95 was prepared as described in Example 18.

Example 19

Preparation of 1-[5-(5-fluoro-pyridin-3-yl)-[1,3,4]thiadiazol-2-yl]-1-methyl-3-(2-methylsulfanyl-ethyl)-urea—(Compound 79)

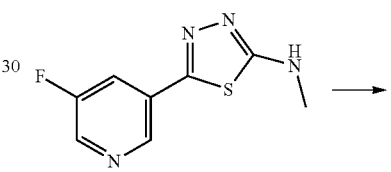

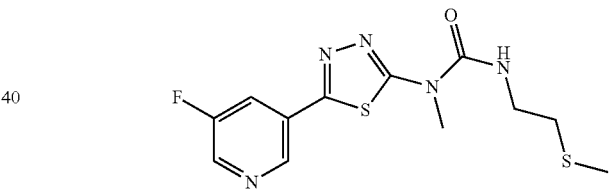

A suspension of methyl-[5-(5-fluoropyridin-3-yl)-[1,3,4]thiadiazol-2-yl]-amine (0.2 g, 0.9 mmol) in ice-cold dichloroethane (3 mL) was treated with a 20% solution of phosgene in toluene (0.52 mL, 1 mmol) and stirred for 10 minutes before the addition of a solution of 4-N,N-dimethylaminopyridine (0.256 g, 2.1 mmol) in dichloroethane (2 mL). The cooling bath was removed after 10 minutes. The reaction mixture was stirred at room temperature for 30 minutes, refluxed under nitrogen for 2 hours, cooled to 1° C. and treated with a solution of 2-methylsulfanyl-ethylamine (91 mg, 1 mmol) in dichloroethane (3 mL) at a dropwise rate via a pipette. The ice bath was removed after 10 minutes and after stirring for 30 minutes at room temperature, the reaction mixture was refluxed under nitrogen for 3 hours, cooled, and diluted with dichloroethane (30 mL). The reaction mixture was washed with dilute hydrochloric acid (0.1N, 2×15 mL), saturated aqueous sodium bicarbonate (30 mL), brine (20 mL), and then dried over MgSO$_4$ and chromatographed on silica to afford the title compound as a white solid (0.26 g, 84%): mp 100-104° C.; $^1$H NMR (400 MHz, CDCl$_3$) δ 8.88 (s, 1H), 8.55 (d, J=2.8 Hz, 1H), 8.02 (ddd, J=8.9, 2.7, 1.7 Hz, 1H), 6.92 (br, 1H), 3.71 (s, 3H), 3.65-3.59 (m, 2H), 2.76 (t, J=6.6 Hz, 2H), 2.16 (s, 3H); ESIMS m/z 328 ([M+H]⁺).

Example 20

Preparation of 1-[5-(5-fluoro-pyridin-3-yl)-[1,3,4]thiadiazol-2-yl]-1,3-dimethyl-3-(2-methylsulfanyl-ethyl)-urea (Compound 83)

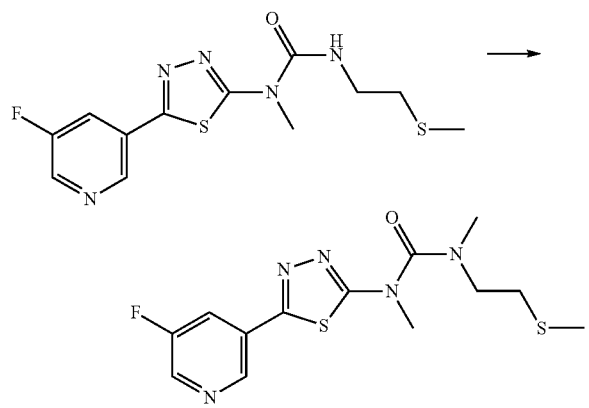

An ice-cold solution of 1-[5-(5-fluoro-pyridin-3-yl)-[1,3,4]thiadiazol-2-yl]-1-methyl-3-(2-methylsulfanyl-ethyl)-urea (0.132 g, 0.4 mmol) in N,N-dimethylformamide (0.6 mL) was treated with sodium hydride (60% in mineral oil, 0.018 g, 0.4 mmol) and stirred for 5 minutes before addition of a solution of iodomethane (0.063 g, 0.4 mmol) in N,N-dimethylformamide (0.1 mL). The ice bath was removed after 5 minutes. The reaction mixture was stirred at room temperature for 14 hours, diluted with water (30 mL) and extracted with EtOAc (3×20 mL). The combined organic extracts were washed with brine (20 mL), dried over MgSO₄, purified by normal and reversed phase chromatography to give the title compound as a colorless gum (0.027 g, 20%): IR (KBr thin film) 1658 cm⁻¹; ¹H NMR (400 MHz, CDCl₃) δ 8.87 (s, 1H), 8.53 (d, J=3.2 Hz, 1H), 8.02 (ddd, J=9.1, 4.5, 1.7 Hz, 1H), 3.66 (s, 3H), 3.59 (t, J=6.8 Hz, 2H), 3.06 (s, 3H), 2.78 (t, J=7.1 Hz, 2H), 2.14 (s, 3H); ESIMS m/z 342 ([M+H]⁺).

Example 21

Synthesis of N-methyl-4-oxo-N-[5-(3-pyridyl)-1,3,4-thiadiazol-2-yl]pentanamide (Compound 49)

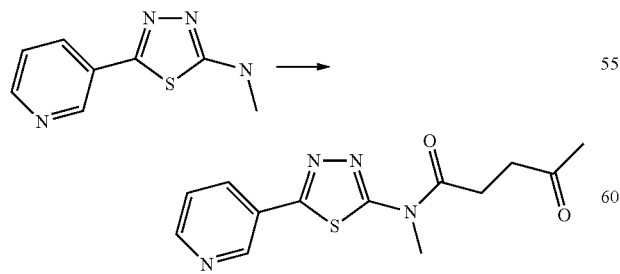

4-oxopentanoyl chloride (0.378 g, 2.8 mmol) was added to a suspension of N-methyl-5-(3-pyridyl)-1,3,4-thiadiazol-2-amine (0.3 g, 1.6 mmol) and 4-N,N-dimethylaminopyridine (0.229 g, 1.9 mmol) in dichloroethane (5 mL), stirred under nitrogen at room temperature for 30 minutes, refluxed for 14 hours, cooled, diluted with dichloroethane (50 mL) and washed with saturated aqueous sodium bicarbonate (70 mL). The aqueous layer was extracted with dichloroethane (30 mL) and the combined organic layers were dried over MgSO₄, adsorbed on silica, applied to a Michel-Miller column and eluted with 9:1 ethyl acetate/hexane. The major fraction was collected and recrystallized from ethyl acetate/hexane to afford yellow needles. Yield 0.21 g (46%): mp 146-147° C.; IR (KBr, thin film) 1701, 1659 cm⁻¹; ¹HNMR (400 MHz, CDCl₃) δ 9.13 (d, J=1.8 Hz, 1H), 8.69 (dd, J=4.8, 1.5 Hz, 1H), 8.28 (dt, J=6.2, 1.9 Hz, 1H), 7.42 (dd, J=8.0, 5.1 Hz, 1H), 3.90 (s, 3H), 2.96 (br, 4H), 2.29 (s, 3H); ESIMS m/z 291 ([M+H]⁺).

Example 22

Preparation of 3-(cyanoamino)-N-methyl-N-[5-(3-pyridyl)-1,3,4-thiadiazol-2-yl]propanamide (Compound 23)

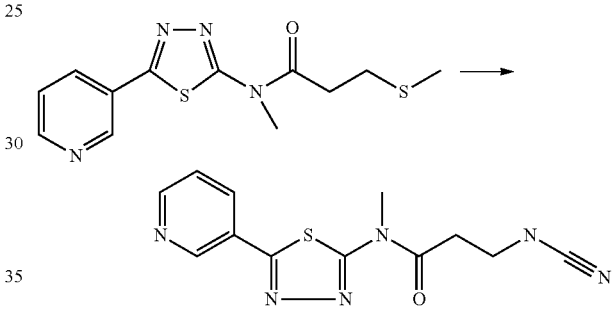

Cyanamide (42 mg, 1.0 mmol) and N-methyl-3-methylsulfanyl-N-[5-(3-pyridyl)-1,3,4-thiadiazol-2-yl]propanamide (294 mg, 1.0 mmol) were suspended in THF and cooled in a −10° C. bath. Iodobenzene diacetate (322 mg, 1.0 mmol) was added and the resulting suspension was stirred at for 4 h. The reaction mixture was concentrated under reduced pressure and purified by reversed phase silica chromatography eluting with an aqueous acetonitrile mobile phase to yield a white solid (84 mg, 29%): mp 155-159° C.; ¹H NMR (300 MHz, CDCl₃) δ 9.15 (m, 1H), 8.72 (m, 1H), 8.35 (m, 1H), 7.45 (m, 1H), 4.70 (bs, 1H), 3.90 (s, 3H), 3.55 (m, 2H), 3.05 (m, 2H); ESIMS m/z 289 ([M+H]⁺).

Example 23

Preparation of 4-[(E)-methoxyimino]-pentanoic acid methyl-(5-pyridin-3-yl-[1,3,4]thiadiazol-2-yl)-amide (Compound 48)

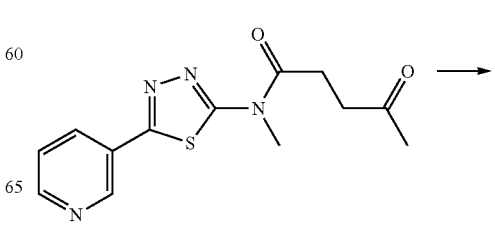

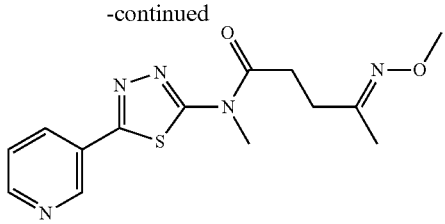

4-[(E)-methoxyimino]-pentanoic acid methyl-(5-pyridin-3-yl-[1,3,4]thiadiazol-2-yl)-amide was prepared as described in J F W Keana et al. in *J. Org. Chem.*, 1985, 50, 2346. A suspension of O-methylhydroxylamine hydrochloride (0.065 g, 0.9 mmol), 4-oxo-pentanoic acid methyl-(5-pyridin-3-yl-[1,3,4]thiadiazol-2-yl)-amide (0.18 g, 0.6 mmol) and sodium acetate (0.076 g, 0.9 mmol) in anhydrous ethanol was refluxed under nitrogen for 14 hours, cooled, concentrated under reduced pressure and chromatographed on silica to afford the title compound as an amorphous yellow solid (0.071 g, 36%): mp 114-121° C.; $^1$H NMR (400 MHz, CDCl$_3$) δ 9.15 (d, J=1.8 Hz, 1H), 8.70 (dd, J=4.8, 1.8 Hz, 1H), 8.29 (dt, J=5.9, 1.8 Hz, 1H), 7.43 (dd, J=7.7, 5.2 Hz, 1H), 3.92 (s, 3H), 3.86, 3.83 and 3.77 (all s, 1H), 2.95 (q, J=7.0 Hz, 2H), 2.71 (q, J=7.4 Hz, 2H), 2.11, 1.98 and 1.89 (all s, 3H); ESIMS m/z 320 ([M+H]$^+$).

Example 24

Preparation of (E)-N-methyl-3-(methylthio)-N-(5-(pyridin-3-yl)-1,3,4-thiadiazol-2-yl)acrylamide (Compound 21)

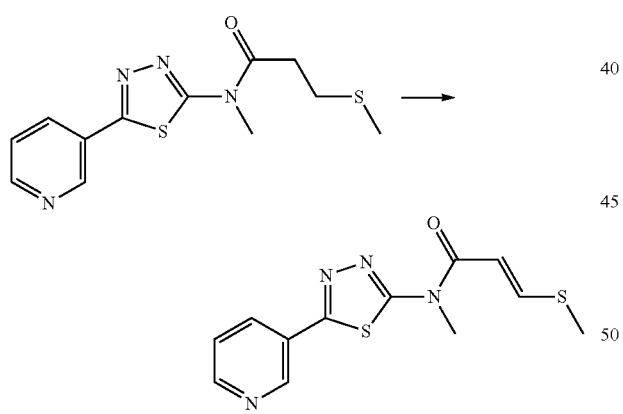

N-Chlorosuccinimide (100 mg, 0.75 mmol, 1.1 equiv) was added to a stirred solution of N-methyl-3-(methylthio)-N-(5-(pyridin-3-yl)-1,3,4-thiadiazol-2-yl)propanamide (200 mg, 0.68 mmol, 1.0 equiv) in benzene (3.3 mL) at 23° C. The resulting cloudy yellow solution was stirred at 23° C. for 30 m. Triethylamine (210 μL, 1.5 mmol, 2.2 equiv) was added and the resulting bright yellow mixture was stirred at 23° C. for 24 h. The reaction mixture was directly subjected to silica gel column chromatography (ethyl acetate) to afford the title compound as a tan powder (80 mg, 40%): $^1$H NMR (300 MHz, DMSO-d$_6$) δ 9.14 (br s, 1H), 8.67 (m, 1H), 8.27 (m, 1H), 8.11 (d, J=14 Hz, 1H), 7.41 (m, 1H), 6.30 (d, J=14 Hz, 1H), 3.91 (s, 3H), 2.46 (s, 3H); ESIMS m/z 293 ([M+H]$^+$).

Example 25

Preparation of N-methyl-N-(5-(pyridin-3-yl)-1,3,4-thiadiazol-2-yl)-3-(tritylthio)propanamide (Compound 22)

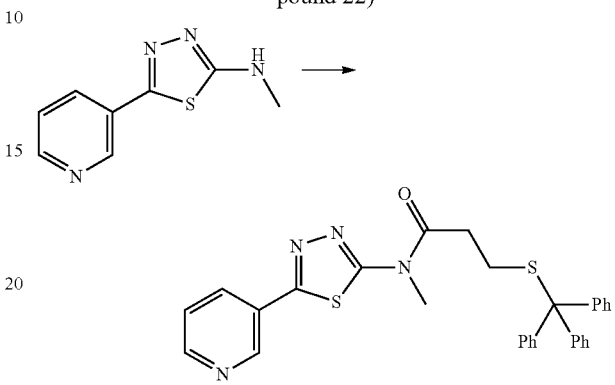

Oxalyl chloride (380 μL, 4.3 mmol, 1.5 equiv) and N,N-dimethylformamide (11 μL, 0.14 mmol, 0.05 equiv) were sequentially added to a stirred suspension of 3-(tritylthio)propanoic acid (1.0 g, 2.9 mmol, 1.0 equiv) in toluene (10 mL) at 23° C. The resulting bubbling white suspension was stirred at 23° C. for 17 h. The reaction mixture was concentrated by rotary evaporation. A portion of the resulting product, 3-(tritylthio)propanoyl chloride (400 mg, 1.1 mmol, 1.1 equiv), was added to a stirred suspension of N-methyl-5-(pyridin-3-yl)-1,3,4-thiadiazol-2-amine (190 mg, 1.0 mmol, 1.0 equiv) and 4-dimethylaminopyridine (150 mg, 1.2 mmol, 1.2 equiv) in dichloromethane (3.0 mL) at 23° C. The resulting yellow solution was stirred at 23° C. for 15 h. The reaction mixture was diluted with a saturated solution of sodium bicarbonate (40 mL) and extracted with ethyl acetate (3×30 mL). The combined organic layers were dried (Na$_2$SO$_4$), gravity-filtered, and concentrated by rotary evaporation. The residue was purified by silica gel column chromatography (ethyl acetate) to afford the title compound as a white foam (450 mg, 87%): mp 60-75° C.; IR (KBr thin film) 3438 (w), 3024 (w), 2909 (w), 2742 (w), 2649 (w), 2565 (w), 1701 (s) cm$^{-1}$; $^1$H NMR (300 MHz, CDCl$_3$) δ 9.12 (d, J=2 Hz, 1H), 8.67 (dd, J=5, 2 Hz, 1H), 8.25 (dt, J=8, 2 Hz, 1H), 7.18-7.50 (m, 16H), 3.58 (s, 3H), 2.73 (t, J=7 Hz, 2H), 2.34 (t, J=7 Hz, 2H); ESIMS m/z 523 ([M+H]$^+$).

Example 26

Preparation of 3-mercapto-N-methyl-N-(5-(pyridin-3-yl)-1,3,4-thiadiazol-2-yl)propanamide (Compound 25)

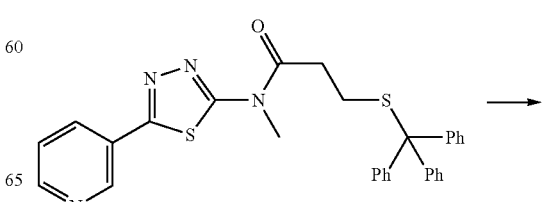

-continued

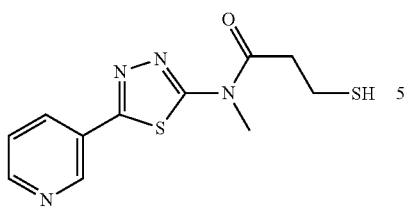

Triethylsilane (76 µL, 0.48 mmol, 5.0 equiv) and trifluoroacetic acid (710 µL, 5.7 mmol, 100 equiv) were sequentially added to a stirred solution of N-methyl-N-(5-(pyridin-3-yl)-1,3,4-thiadiazol-2-yl)-3-(tritylthio)propanamide (50 mg, 0.096 mmol, 1.0 equiv) in dichloromethane (1.3 mL) at 23° C. The resulting solution was stirred at 23° C. for 30 m. The reaction mixture was diluted with a saturated solution of sodium bicarbonate (40 mL) and extracted with ethyl acetate (3×30 mL). The combined organic layers were dried (Na$_2$SO$_4$), gravity-filtered, and concentrated by rotary evaporation. The residue was purified by silica gel column chromatography (ethyl acetate) to afford the title compound as a white powder (23 mg, 85%): mp 149-151° C.; $^1$H NMR (300 MHz, CDCl$_3$) δ 9.17 (br s, 1H), 8.71 (m, 1H), 8.29 (m, 1H), 7.44 (dd, J=8, 5 Hz, 1H), 3.87 (s, 3H), 2.91-310 (m, 4H), 1.87 (t, J=8 Hz, 1H); ESIMS m/z 281 ([M+H]$^+$).

Example 27

Preparation of S-3-(methyl(5-(pyridin-3-yl)-1,3,4-thiadiazol-2-yl)-amino)-3-oxopropyl ethanethioate (Compound 26)

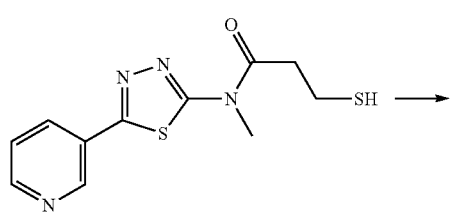

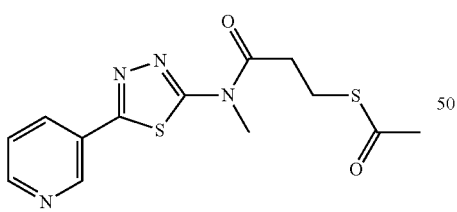

Triethylamine (12 µL, 0.086 mmol, 1.2 equiv) and acetyl chloride (6 µL, 0.08 mmol, 1 equiv) were sequentially added to a stirred solution of 3-mercapto-N-methyl-N-(5-(pyridin-3-yl)-1,3,4-thiadiazol-2-yl)propanamide (20 mg, 0.071 mmol, 1.0 equiv) in 1,2-dichloroethane (1.4 mL) at 23° C. The resulting pale yellow solution was stirred at 23° C. for 16 h. The reaction mixture was directly subjected to silica gel column chromatography (ethyl acetate) to afford the title compound as a white powder (23 mg, 99%): mp 133-135° C.; $^1$H NMR (300 MHz, CDCl$_3$) δ 9.14 (d, J=2 Hz, 1H), 8.69 (dd, J=5, 2 Hz, 1H), 8.27 (dt, J=8, 2 Hz, 1H), 7.42 (dd, J=8, 5 Hz, 1H), 3.82 (s, 3H), 3.26 (t, J=7 Hz, 2H), 3.03 (t, J=7 Hz, 2H), 2.36 (s, 3H); ESIMS m/z 323 ([M+H]$^+$).

Example 28

Preparation of N-methyl-N-(5-(pyridin-3-yl)-1,3,4-thiadiazol-2-yl)-3-(trifluoromethylthio)propanamide (Compound 27)

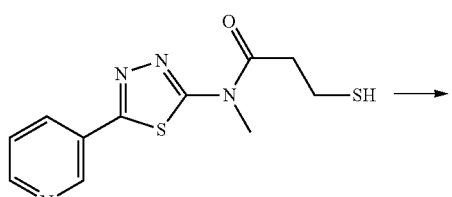

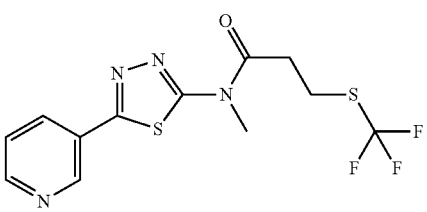

A 2M solution of sodium hydroxide (40 µL, 0.078 mmol, 1.1 equiv) was added to a stirred suspension of 3-mercapto-N-methyl-N-(5-(pyridin-3-yl)-1,3,4-thiadiazol-2-yl)propanamide (20 mg, 0.071 mmol, 1.0 equiv) in acetonitrile (2.1 mL) at 23° C. Gaseous trifluoromethyl iodide was bubbled into the resulting solution at a steady rate for 5 m. The glass reaction vessel was sealed and the resulting cloudy pale yellow solution was exposed to a Sylvania sun lamp at a distance of ~6 inches for 2 h. The reaction mixture was diluted with water (20 mL) and extracted with ethyl acetate (3×20 mL). The combined organic layers were dried (MgSO$_4$), gravity-filtered, and concentrated by rotary evaporation. The residue was purified by silica gel column chromatography (ethyl acetate) to afford a yellow film (6 mg, 24% yield): $^1$H NMR (300 MHz, CDCl$_3$) δ 9.15 (d, J=2 Hz, 1H), 8.70 (dd, J=5, 2 Hz, 1H), 8.28 (dt, J=8, 2 Hz, 1H), 7.43 (dd, 1H, J=8, 5 Hz, 1H), 3.86 (s, 3H), 3.30 (t, J=7 Hz, 2H), 3.16 (t, J=7 Hz, 2H); ESIMS m/z 349 ([M+H]$^+$).

Example 29

Preparation of N-2,2-trimethyl-3-(methyl-N-cyanosulfiliminyl)-N-(5-(pyridin-3-yl)-1,3,4-thiadiazol-2-yl)propanamide (Compound 39)

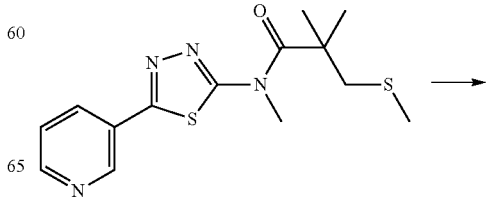

-continued

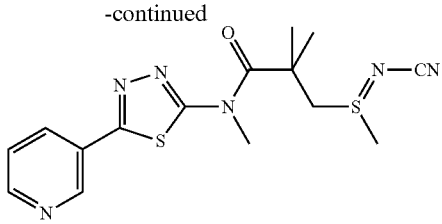

Cyanamide (8 mg, 0.19 mmol, 1.2 equiv) and iodobenzene diacetate (55 mg, 0.17 mmol, 1.1 equiv) were sequentially added to a stirred solution of N,2,2-trimethyl-3-(methylthio)-N-(5-(pyridin-3-yl)-1,3,4-thiadiazol-2-yl)propanamide (50 mg, 0.16 mmol, 1.0 equiv) in 1,4-dioxane (2.0 mL) at 23° C. The resulting solution was stirred at 23° C. for 3 h. The reaction mixture was diluted with a saturated solution of sodium bicarbonate (40 mL) and extracted with dichloromethane (3×30 mL). The combined organic layers were dried (Na$_2$SO$_4$), gravity-filtered, and concentrated by rotary evaporation. The residue was dissolved in acetonitrile (30 mL) and washed with hexane (5×20 mL). The acetonitrile layer was concentrated by rotary evaporation to afford the title compound as a white foam (56 mg, 99%): mp 42-52° C.; IR (KBr thin film) 2994 (w), 2143 (s), 1638 (m) cm$^{-1}$; $^1$H NMR (300 MHz, CDCl$_3$) δ 9.13 (d, J=2 Hz, 1H), 8.72 (dd, J=5, 2 Hz, 1H), 8.31 (dt, J=8, 2 Hz, 1H), 7.44 (dd, J=8, 5 Hz, 1H), 4.00 (s, 3H), 3.59 (d, J=13 Hz, 1H), 3.24 (d, J=13 Hz, 1H), 3.09 (s, 3H), 1.88 (s, 3H), 1.66 (s, 3H); ESIMS m/z 363 ([M+H]$^+$).

Example 30

Preparation of 2-(aminomethyl)-N-[5-(5-fluoro-3-pyridyl)-1,3,4-thiadiazol-2-yl]-N,2-dimethyl-3-methylsulfanyl-propanamide (Compound 89)

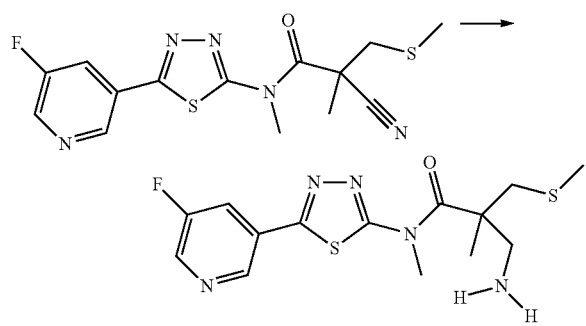

A suspension of 2-cyano-N-[5-(5-fluoro-3-pyridyl)-1,3,4-thiadiazol-2-yl]-N,2-dimethyl-3-methylsulfanyl-propanamide (157 mg, 0.4 mmol) and platinum oxide (131 mg, 0.6 mmol) in glacial acetic acid (8 mL) was reduced under 45 psi of hydrogen at room temperature for 16 hours, filtered through Celite and concentrated under reduced pressure. The residue was treated with saturated aqueous sodium bicarbonate (30 mL) and extracted with ethyl acetate (3×50 mL). Organic extracts were concentrated under reduced pressure and purified by reversed phase silica chromatography eluting with an aqueous acetonitrile mobile phase. Yield 33 mg (21%): mp 154-157° C.; IR (KBr thin film) 1656, 1383 cm$^{-1}$; $^1$H NMR (400 MHz, CDCl$_3$) δ 11.17 (br, 1H), 9.02 (t, J=1.6 Hz, 1H), 8.43 (d, J=2.8 Hz, 1H), 8.11 (ddd, J=9.8, 2.8, 1.8 Hz, 1H), 3.87 (d, J=2.9 Hz 1H), 3.48 (s, 3H), 3.47 (d, J=2.9 Hz, 1H), 2.99 (d, J=12.7 Hz, 1H), 2.78 (d, J=13.6 Hz, 1H), 2.20 (s, 3H), 1.41 (s, 3H); ESIMS (m/z) 356 [M+H]$^+$.

Example 31

Preparation of 3-amino-N-methyl-N-(5-(pyridin-3-yl)-1,3,4-thiadiazol-2-yl)propanamide (Compound 41)

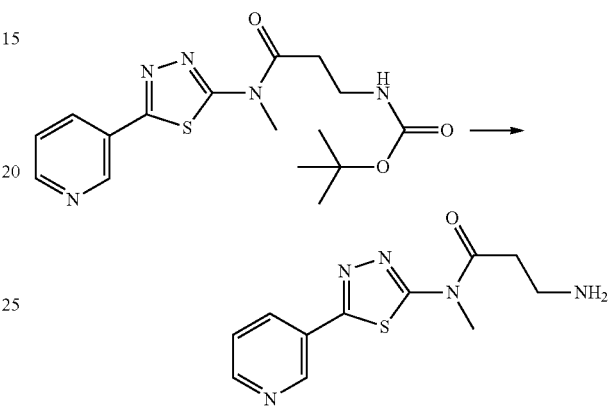

Triethylsilane (530 μL, 3.3 mmol, 5.0 equiv) and trifluoroacetic acid (4.9 mL, 66 mmol, 100 equiv) were sequentially added to a stirred solution of tert-butyl 3-(methyl(5-(pyridin-3-yl)-1,3,4-thiadiazol-2-yl)amino)-3-oxopropylcarbamate (240 mg, 0.66 mmol, 1.0 equiv) in dichloromethane (8.8 mL) at 23° C. The resulting colorless solution was stirred at 23° C. for 30 m. The reaction mixture was concentrated by rotary evaporation. The residue was diluted with a saturated solution of sodium bicarbonate (80 mL) and extracted with dichloromethane (8×50 mL). The combined organic layers were dried (Na$_2$SO$_4$), gravity filtered, and concentrated by rotary evaporation to afford the title compound as a tan powder (86 mg, 49%): mp 110-112° C.; IR (KBr thin film) 3047 (w), 2926 (w), 1682 (s), 1591 (m) cm$^{-1}$; $^1$H NMR (300 MHz, CDCl$_3$) δ 9.15 (d, J=2 Hz, 1H), 8.69 (dd, J=5, 2 Hz, 1H), 8.28 (dt, J=8, 2 Hz, 1H), 7.43 (dd, J=8, 5 Hz, 1H), 3.86 (s, 3H), 3.17 (m, 2H), 2.86 (t, J=6 Hz, 2H); ESIMS m/z 264 ([M+H]$^+$).

Example 32

Preparation of N-2,2-trimethyl-3-(methyl-N-cyano-sulfoximinyl)-N-(5-(pyridin-3-yl)-1,3,4-thiadiazol-2-yl)propanamide (Compound 42)

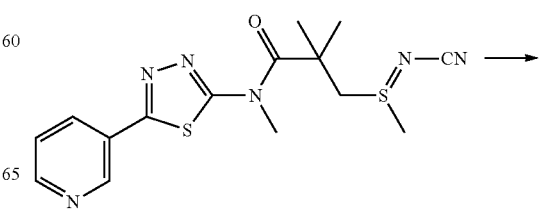

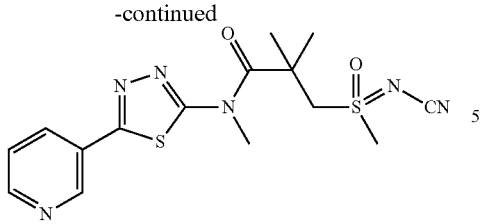

A solution of N,2,2-trimethyl-3-(methyl-N-cyano-sulfiliminyl)-N-(5-(pyridin-3-yl)-1,3,4-thiadiazol-2-yl)propanamide (100 mg, 0.29 mmol, 1.0 equiv) in absolute ethanol (2.0 mL) was added to a stirred suspension of powdered potassium carbonate (87 mg, 0.63 mmol, 2.2 equiv) and meta-chloroperoxybenzoic acid (73 mg, 0.32 mmol, 1.1 equiv) in water (1.0 mL) at 23° C. The resulting yellow solution was stirred at 23° C. for 1 h. The reaction mixture was diluted with a saturated solution of sodium bicarbonate (40 mL) and extracted with dichloromethane (3×30 mL). The combined organic layers were dried (Na$_2$SO$_4$), gravity-filtered, and concentrated by rotary evaporation. The residue was purified by silica gel column chromatography (ethyl acetate) to afford the title compound as a white foam (36 mg, 33%): IR (KBr thin film) 2992 (w), 2926 (w), 2192 (s), 1649 (s) cm$^{-1}$; $^1$H NMR (300 MHz, CDCl$_3$) δ 9.12 (br s, 1H), 8.70 (dd, J=5 Hz, 1H), 8.29 (dt, J=8, 2 Hz, 1H), 7.43 (dd, J=8, 5 Hz, 1H), 4.21 (d, J=14 Hz, 1H), 3.97 (s, 3H), 3.68 (d, J=14 Hz, 1H), 3.53 (s, 3H), 1.92 (s, 3H), 1.63 (s, 3H); ESIMS m/z 379 ([M+H]$^+$).

Example 33

Preparation of 2-(methylthiomethyl)-3-phenylpropanoic acid

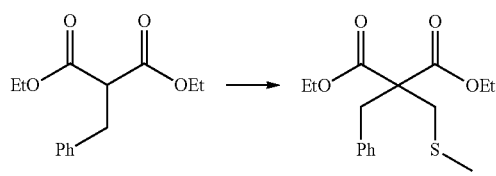 [SMILES: CCOC(=O)C(Cc1ccccc1)C(=O)OCC ; CCOC(=O)C(CSC)(Cc1ccccc1)C(=O)OCC]

Preparation of diethyl 2-benzyl-2-(methylthiomethyl)malonate

Chloromethyl methyl sulfide (1.4 mL, 17 mmol, 1.0 equiv) and 60% sodium hydride in mineral oil (750 mg, 19 mmol, 1.1 equiv) were sequentially added to a stirred solution of diethyl 2-benzylmalonate (4.0 mL, 17 mmol, 1.0 equiv) in N,N-dimethylformamide (34 mL) at 0° C. The resulting mixture was warmed to 23° C. and stirred for 18 h. The reaction mixture was concentrated under vacuum. The residue was diluted with water (150 mL) and extracted with diethyl ether (4×70 mL). The combined organic layers were dried (MgSO$_4$), gravity-filtered, and concentrated by rotary evaporation to afford a yellow oil (5.3 g, 99%): $^1$H NMR (300 MHz, CDCl$_3$) δ 7.13-7.30 (m, 5H), 4.22 (q, J=7 Hz, 4H), 3.36 (s, 2H), 2.94 (s, 2H), 2.11 (s, 3H), 1.27 (t, J=7 Hz, 6H).

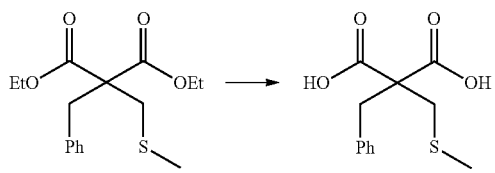 [SMILES: CCOC(=O)C(CSC)(Cc1ccccc1)C(=O)OCC ; CSCC(Cc1ccccc1)(C(=O)O)C(=O)O]

Preparation of 2-benzyl-2-(methylthiomethyl)malonic acid

Powdered potassium hydroxide (4.8 g, 86 mmol, 5.0 equiv) was added to a stirred solution of diethyl 2-benzyl-2-(methylthiomethyl)malonate (5.3 g, 17 mmol, 1.0 equiv) in 3:1 methanol:water (28 mL) at 23° C. The resulting pale yellow suspension was heated to 100° C. and stirred for 4 h. The cooled reaction mixture was acidified to pH≈9 with concentrated hydrochloric acid and washed with diethyl ether (4×50 mL). The aqueous layer was acidified to pH≈1 with concentrated hydrochloric acid and extracted with dichloromethane (4×60 mL). The combined organic layers were dried (Na$_2$SO$_4$), gravity-filtered, and concentrated by rotary evaporation to afford the title compound as a white powder (3.1 g, 72%): $^1$H NMR (300 MHz, DMSO-d$_6$) δ 7.13-7.34 (m, 5H), 3.15 (s, 2H), 2.73 (s, 2H), 2.08 (s, 3H).

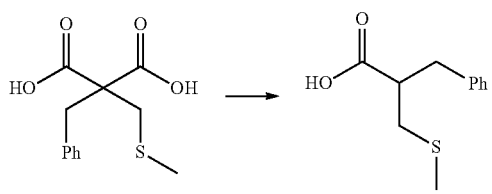 [SMILES: CSCC(Cc1ccccc1)(C(=O)O)C(=O)O ; CSCC(Cc1ccccc1)C(=O)O]

Preparation of 2-(methylthiomethyl)-3-phenylpropanoic acid

2-Benzyl-2-(methylthiomethyl)malonic acid (3.1 g, 12 mmol, 1.0 equiv) was placed in a 50 mL round bottom flask and heated to 170° C. via heating mantle. The resulting liquid was heated neat for 1 h, until bubbling had ceased. The residue was cooled to afford the title compound as an off-white powder (2.6 g, 99%): $^1$H NMR (300 MHz, DMSO-d$_6$) δ 12.36 (br s, 1H), 7.16-7.33 (m, 5H), 2.74-2.88 (m, 3H), 2.52-2.69 (m, 2H), 2.04 (s, 3H).

Example 34

Preparation of 1-(methylthiomethyl)cyclopropanecarboxylic acid

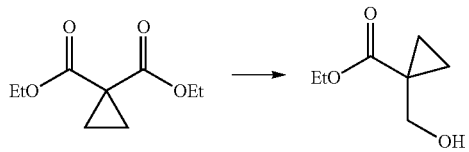 [SMILES: CCOC(=O)C1(C(=O)OCC)CC1 ; CCOC(=O)C1(CO)CC1]

Preparation of ethyl 1-(hydroxymethyl)cyclopropanecarboxylate

A 1M solution of lithium aluminum tri-tert-butoxyhydride in tetrahydrofuran (12 mL, 12 mmol, 2.2 equiv) was added to a stirred solution of diethyl cyclopropane-1,1'-dicarboxylate (1.0 mL, 5.7 mmol, 1.0 equiv) in tetrahydrofuran (19 mL) at 23° C. The resulting solution was heated to 65° C. and stirred for 24 h. The cooled reaction mixture was diluted with a 10% solution of sodium bisulfate (100 mL) and extracted with ethyl acetate (4×50 mL). The combined organic layers were dried (MgSO$_4$), gravity-filtered, and concentrated by rotary evaporation to afford the title compound as a pale yellow oil (850 mg, 88%): $^1$H NMR (300 MHz, CDCl$_3$) δ 4.16 (q, J=7 Hz, 2H), 3.62 (s, 2H), 2.60 (br s, 1H), 1.22-1.30 (m, 5H), 0.87 (dd, J=7, 4 Hz, 2H).

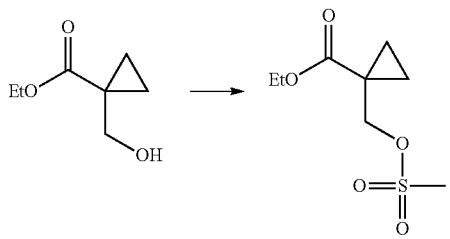

Preparation of ethyl 1-((methylsulfonyloxy)methyl)cyclopropanecarboxylate

Triethylamine (990 µL, 7.1 mmol, 1.2 equiv) and methanesulfonyl chloride (500 µL, 6.5 mmol, 1.1 equiv) were sequentially added to a stirred solution of ethyl 1-(hydroxymethyl)cyclopropanecarboxylate (840 mg, 5.7 mmol, 1.0 equiv) in dichloromethane (15 mL) at 23° C. The resulting bright yellow solution was stirred at 23° C. for 20 h. The reaction mixture was diluted with water (100 mL) and extracted with dichloromethane (3×50 mL). The combined organic layers were dried (MgSO$_4$), gravity-filtered, and concentrated by rotary evaporation to afford the title compound as a brown oil (1.1 g, 85%): $^1$H NMR (300 MHz, CDCl$_3$) δ 4.33 (s, 2H), 4.16 (q, J=7 Hz, 2H), 3.08 (s, 3H), 1.43 (dd, J=7, 4 Hz, 2H), 1.26 (t, J=7 Hz, 3H), 1.04 (dd, J=7, 4 Hz, 2H).

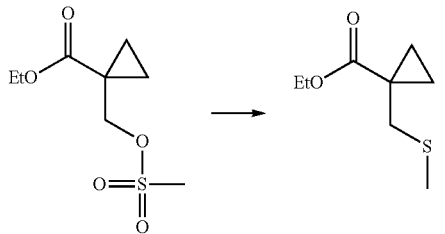

Preparation of ethyl 1-(methylthiomethyl)cyclopropanecarboxylate

Sodium methanethiolate (700 mg, 9.9 mmol, 2.0 equiv) was added to a stirred solution of ethyl 1-((methylsulfonyloxy)methyl)cyclopropanecarboxylate (1.1 g, 4.9 mmol, 1.0 equiv) in N,N-dimethylformamide (10 mL) at 23° C. The resulting brown suspension was stirred at 23° C. for 18 h. The reaction mixture was diluted with water (500 mL) and extracted with diethyl ether (4×100 mL). The combined organic layers were dried (MgSO$_4$), gravity-filtered, and concentrated by rotary evaporation to afford the title compound as a brown oil (860 mg, 99%): $^1$H NMR (300 MHz, CDCl$_3$) δ 4.14 (q, J=7 Hz, 2H), 2.83 (s, 2H), 2.16 (s, 3H), 1.31 (dd, J=7, 4 Hz, 2H), 1.25 (t, J=7 Hz, 3H), 0.89 (dd, J=7, 4 Hz, 2H).

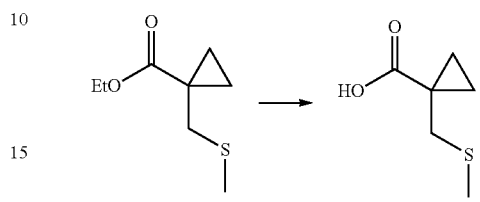

Preparation of 1-(methylthiomethyl)cyclopropanecarboxylic acid

A 50% solution of sodium hydroxide (2.0 mL, 38 mmol, 7.8 equiv) was added to a stirred solution of ethyl 1-(methylthiomethyl)cyclopropanecarboxylate (860 mg, 4.9 mmol, 1.0 equiv) in absolute ethanol (10 mL) at 23° C. The resulting solution was stirred at 23° C. for 20 h. The reaction mixture was diluted with a 0.5M solution of sodium hydroxide (100 mL) and washed with dichloromethane (3×100 mL). The aqueous layer was acidified to pH≈1 with concentrated hydrochloric acid and extracted with dichloromethane (4×100 mL). The combined organic layers were dried (Na$_2$SO$_4$), gravity-filtered, and concentrated by rotary evaporation to afford a light brown oil (420 mg, 58%): $^1$H NMR (300 MHz, CDCl$_3$) δ 2.82 (s, 2H), 2.17 (s, 3H), 1.41 (dd, J=7, 4 Hz, 2H), 0.99 (dd, J=7, 4 Hz, 2H).

2-Ethyl-2-[(methylthio)methyl]butanoic acid was prepared as described in Example 34.

Example 35

Preparation of 2-methyl-3-(methylthio)propanoic acid

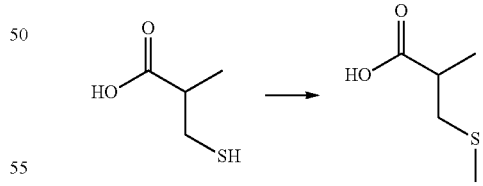

Powdered potassium hydroxide (1.0 g, 18 mmol, 2.2 equiv) and iodomethane (570 µL, 9.2 mmol, 1.1 equiv) were sequentially added to a stirred solution of 3-mercapto-2-methylpropanoic acid (1.0 g, 8.3 mmol, 1.0 equiv) in methanol (3.7 mL) at 23° C. The resulting white suspension was heated to 65° C. and stirred for 2 h. The cooled reaction mixture was diluted with a 1M solution of hydrochloric acid (50 mL) and extracted with ethyl acetate (2×50 mL). The combined organic layers were dried (Na$_2$SO$_4$), gravity-filtered, and concentrated by rotary evaporation to afford the title compound as a yellow oil (1.0 g, 91%): $^1$H NMR (300 MHz, CDCl$_3$) δ 2.70-2.89 (m, 2H), 2.57 (dd, J=12, 6 Hz, 1H), 2.13 (s, 3H), 1.30 (d, J=7 Hz, 3H).

Example 36

Preparation of 2,2-dimethyl-3-(methylthio)propanoic acid

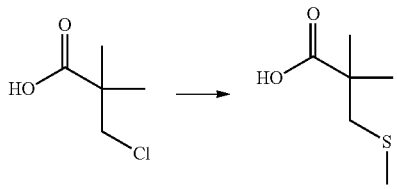

Sodium methanethiolate (1.0 g, 14 mmol, 2.0 equiv) was added to a stirred solution of 3-chloro-2,2-dimethylpropanoic acid (1.0 g, 7.2 mmol, 1.0 equiv) in N,N-dimethylformamide (3.7 mL) at 0° C. The resulting brown suspension was allowed to warm to 23° C. and stirred for 24 h. The reaction mixture was diluted with a saturated solution of sodium bicarbonate (300 mL) and washed with diethyl ether (3×75 mL). The aqueous layer was acidified to pH≈1 with concentrated hydrochloric acid and extracted with diethyl ether (3×75 mL). The combined organic layers were dried (Na$_2$SO$_4$), gravity-filtered, and concentrated by rotary evaporation to afford the title compound as a colorless oil (1.2 g, 99%): $^1$H NMR (300 MHz, CDCl$_3$) δ 2.76 (s, 2H), 2.16 (s, 3H), 1.30 (s, 6H).

Example 37

Preparation of 3-(tritylthio)propanoic acid

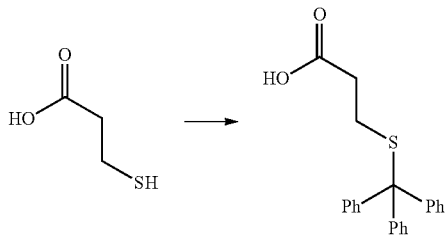 [SMILES: O=C(O)CCS ; O=C(O)CCSC(c1ccccc1)(c1ccccc1)c1ccccc1]

Triphenylmethyl chloride (2.7 g, 9.5 mmol, 1.0 equiv) was added to a stirred solution of 3-thiopropanoic acid (1.0 g, 9.5 mmol, 1.0 equiv) in N,N-dimethylformamide (15 mL) at 23° C. The resulting colorless solution was stirred at 23° C. for 17 h. The reaction mixture was diluted with water (300 mL) and extracted with diethyl ether (4×150 mL). The combined organic layers were diluted with dichloromethane (100 mL) and methanol (100 mL) in order to dissolve all solids, dried (MgSO$_4$), gravity filtered, and concentrated by rotary evaporation. The residue was rinsed with dichloromethane and vacuum-filtered to afford the title compound as white crystals (2.9 g, 88%): mp 205-208° C.; IR (KBr thin film) 3438 (w), 3024 (w), 2909 (w), 2742 (w), 2649 (w), 2565 (w), 1701 (s) cm$^{-1}$; $^1$H NMR (300 MHz, DMSO-d$_6$) δ 12.24 (br s, 1H), 7.20-7.40 (m, 15H), 2.28 (t, J=7 Hz, 2H), 2.16 (t, J=7 Hz, 2H); ESIMS m/z 347 ([M−H]$^-$).

Example 38

Preparation of 3-(tert-Butyl-dimethyl-silanyloxy)-2,2-dimethyl-propionic acid

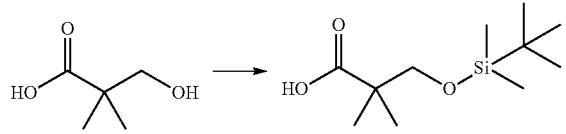

3-(tert-Butyl-dimethyl-silanyloxy)-2,2-dimethyl-propionic acid can be prepared from 3-hydroxy-2,2-dimethylpropanoic acid as described in *Bioorganic & Medicinal Chemistry Letters*. 2004, 14(12), 3231.

Example 39

Preparation of 3-{[2,2-dimethyl-3-(methylthio)propanoyl]oxy}-2,2-dimethylpropanoic acid 3-{[2,2-dimethyl-3-(methylthio)propanoyl]oxy}-2,2-dimethylpropanoic acid can be prepared from 3-hydroxy-2,2-dimethylpropanoic acid as described in Goel, et al. U.S. Patent Application Publication 2005/101572 A1.

Example 40

Preparation of 4-oxopentanoyl chloride

4-Oxopentanoyl chloride was prepared from 4-oxopentanoic acid as described by Tanaka et al. *Biochim Biophys Acta*, 1993, 1166, 264. The desired product was isolated as a yellow liquid in 92% yield: $^1$H NMR (300 MHz, CDCl$_3$) δ 3.00-2.92

(m, 1H), 2.77-2.71 (m, 1H), 2.66-2.59 (m, 1H), 2.46-2.39 (m, 1H), 2.07 (s, 3H); EIMS m/z 131 ([M+H]+).

Example 41

Preparation of ethyl 2-cyano-2-methyl-3-methylsulfanyl-propanoate

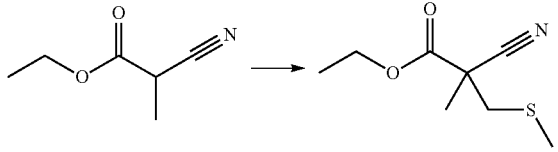

n-Butyllithium (24.2 mL, 60 mmol, 2.5 M solution in hexanes) was added to a solution of iso-propylamine (8.1 mL, 58 mmol) in dry ether (70 mL) under nitrogen at a rate needed to maintain temperature below −60° C. Upon completion, the reaction was allowed to warm to 10° C., re-cooled to −78° C. before addition of ethyl 2-cyanopropanoate (7 g, 55 mmol). After stirring at −78° C. for 90 minutes, chloromethylsulfide (4.61 mL, 55 mmol) was added and the mixture was warmed to room temperature over 14 hours, diluted with ether (350 mL), washed with water (100 mL), brine (100 mL), dried over MgSO$_4$, concentrated under reduced pressure and distilled at 0.04 mm Hg. Yield of yellow liquid 3.95 g. (38%): by 145° C.; IR (KBr thin film) 1751 cm$^{-1}$; $^1$H NMR (400 MHz, CDCl$_3$) δ 4.30 (q, J=7.1 Hz, 2H), 3.08 (d, J=13.9 Hz, 1H), 2.91 (d, J=13.9 Hz, 1H), 2.30 (s, 3H), 1.67 (s, 3H), 1.35 (t, J=7.4 Hz, 3H); EIMS m/z 187.

Example 42

Preparation of 2-cyano-2-methyl-3-methylsulfanyl-propanoic acid

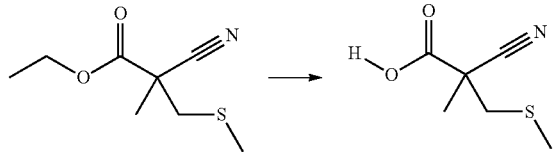

Ethyl 2-cyano-2-methyl-3-methylsulfanyl-propanoate (2.3 g, 12.3 mmol) was added to ice-cold sodium hydroxide (5 mL, 2N) under stirring. Methanol (10 mL) was added and the ice bath removed after an hour. After 45 minutes at room temperature, volatiles were removed under reduced pressure and the residue diluted with water (20 mL). Impurities were removed by ether extraction (2×30 mL). The aqueous layer was cooled in ice, acidified to pH 3 with dilute HCl and extracted with ethyl acetate (3×30 mL). Combined organic extracts were dried over MgSO$_4$ and concentrated under reduced pressure to leave a brown gum. Yield 1.32 g (68%): IR (KBr thin film) 1735 cm$^{-1}$; $^1$H NMR (400 MHz, CDCl$_3$) δ 10.19 (br, 1H), 3.10 (d, J=14.2 Hz, 1H), 2.94 (d, J=13.9 Hz, 1H), 2.33 (s, 3H), 1.73 (s, 3H); $^{13}$C NMR (400 MHz, CDCl$_3$) δ 173.33, 118.82, 45.86, 41.66, 23.05, 17.62.

Example 43

Preparation of 3-allylsulfanyl-2-methyl-propanoic acid

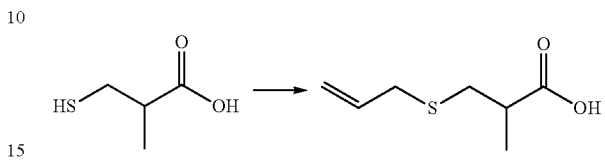

3-Allylsulfanyl-2-methyl-propanoic acid was prepared as described by Zhou et al. J. Org. Chem. 2004, 69, 7072. An ice-cold mixture of 2-methyl-3-sulfanyl-propanoic acid (5 g, 42 mmol) and sodium hydroxide (3.33 g, 83 mmol) in water (50 mL) was treated with a solution of allyl bromide (5.98 g, 49 mmol) in ethanol (100 mL) over 30 minutes. Ice bath was removed after 45 minutes and after 14 hours at room temperature, volatiles were removed under reduced pressure. The residue was cooled in ice, acidified to pH 6 with 1N HCl and extracted with ethyl acetate, washed with water, dried over MgSO$_4$, concentrated under reduced pressure and dried in vacuo at room temperature for 14 hours to leave a clear liquid. Acidification of the aqueous layer to pH 4 afforded an additional 2.7 g of material. Total yield 4.44 g (74%): IR (KBr thin film) 1708 cm$^{-1}$; $^1$H NMR (400 MHz, CDCl$_3$) δ 5.83-5.73 (m, 1H), 5.14-5.13 (m, 1H), 5.10-5.09 (m, 1H), 3.15 (d, J=7.3 Hz, 2H), 2.80 (dd, J=13.2, 7.0 Hz, 2H), 2.69 (sextet, J=7.1 Hz, 1H), 2.53 (dd, J=12.8, 6.5 Hz, 1H), 1.28 (d, J=7.1 Hz, 3H); $^{13}$C NMR (400 MHz, CDCl$_3$) δ 179.01, 131.63, 114.92, 37.38, 32.72, 31.00, 14.19; EIMS m/z 160.

Example 44

Preparation of 3-((benzyloxycarbonyl)(methyl)amino)propanoic acid

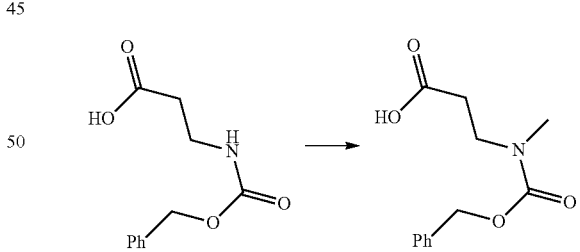

3-((benzyloxycarbonyl)(methyl)amino)propanoic acid was prepared from 3-(benzyloxycarbonylamino)propanoic acid as described by Lerchen et al., PCT Int. Appl. 2007/WO2007093328 A1.

Example 45

Insecticidal Test for Green Peach Aphid (*Myzus persicae*) in Foliar Spray Assay Green peach aphid (MYZUPE) is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. MYZUPE attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. MYZUPE also attacks many ornamental crops such as carnation, chrysanthemum, flowering white cabbage, poinsettia, and roses. MYZUPE has developed resistance to many pesticides.

Certain molecules disclosed in this document were tested against MYZUPE using procedures described in the following example. In the reporting of the results, the "MYZUPE, APHIGO and BEMITA Rating Table" was used (See Table Section).

Cabbage seedlings grown in 3-inch pots, with 2-3 small (3-5 cm) true leaves, were used as test substrate. The seedlings were infested with 20-50 green peach aphids (wingless adult and nymph stage) one day prior to chemical application. Four pots with individual seedlings were used for each treatment. Compounds (2 mg) were dissolved in 2 mL of acetone/methanol (1:1) solvent, forming stock solutions of 1000 ppm. The stock solutions were diluted 5× with 0.025% Tween 20 in $H_2O$ to obtain the test solution at 200 ppm. A hand-held Devilbiss sprayer was used for spraying a solution to both sides of cabbage leaves until runoff. Reference plants (solvent check) were sprayed with the diluent only. Treated plants were held in a holding room for three days at approximately 25° C. and 40% relative humidity (RH) prior to grading. Evaluation was conducted by counting the number of live aphids per plant under a microscope. Insecticidal activity data presented in Table 3 were generated by using Abbott's correction formula:

Corrected%Control=$100*(X-Y)/X$ where X=No. of live aphids on solvent check plants
Y=No. of live aphids on treated plants Example 46

Insecticidal Test for Cotton Aphid (*Aphis gossypii*) in a Foliar Spray Assay

Squash or cotton seedlings with fully expanded cotyledon leaves were trimmed to one cotyledon per plant and infested with wingless adult and nymph stage cotton aphid (APHIGO) one day prior to chemical application. Each plant was examined before chemical application to ensure uniform infestation (ca. 30-70 aphids per plant). Compounds (2 mg) were dissolved in 2 mL of acetone/methanol (1:1) solvent, forming stock solutions of 1000 ppm. The stock solutions were diluted 5× with 0.025% Tween 20 in $H_2O$ to obtain a solution at 200 ppm. A hand-held Devilbiss aspirator type sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for three days at approximately 25° C. and 40% RH before the number of live cotton aphids on each plant was recorded. Insecticidal activity data presented in Table 3 were generated by using Abbott's correction formula:

Corrected%Control=$100*(X-Y)/X$ where X=No. of live aphids on solvent check plants
Y=No. of live aphids on treated plants Example 47

Insecticidal Test for Sweetpotato Whitefly (*Bemisia tabaci*) in Foliar Spray Assay Cotton plants were used as test substrate and were grown in 3-inch pots and pruned until only 1 small (3-5 cm) true leaf remained. The plants were then placed in a room with whitefly (BEMITA) adults and allowed to be infested with eggs. After a 2-3 day egg-laying period, plants were taken from the adult whitefly room and the adults were removed from the leaves using compressed air delivered through a hand-held Devilbiss sprayer (23 psi). Plants infested with eggs (100-300 eggs per plant) were placed in a controlled-environment room for 5-6 days at 82° F. and 50% RH until approximately 50% egg hatch. Four cotton plants (4 replicates) were used for each treatment. Compounds (2 mg) were dissolved in 1 mL of acetone solvent, forming stock solutions of 2000 ppm. The stock solutions were diluted 10× with 0.025% Tween 20 in $H_2O$ to obtain the test solution of 200 ppm. A hand-held Devilbiss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity data presented in Table 3 were generated by using Abbott's correction formula:

Corrected%Control=$100*(X-Y)/X$ where X=No. of live nymphs on solvent check plants
Y=No. of live nymphs on treated plants Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures.

Insecticides

Molecules of Formula One may also be used in combination (such as, in a compositional mixture, or a simultaneous or sequential application) with one or more of the following insecticides—1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos (collectively these commonly named insecticides are defined as the "Insecticide Group").

Acaricides

Molecules of Formula One may also be used in combination (such as, in a compositional mixture, or a simultaneous or sequential application) with one or more of the following acaricides—acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorobenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfuram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfuram, sulfur, tetradifon, tetranactin, tetrasul, and thioquinox (collectively these commonly named acaricides are defined as the "Acaricide Group").

Nematicides

Molecules of Formula One may also be used in combination (such as, in a compositional mixture, or a simultaneous or sequential application) with one or more of the following nematicides—1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, and thionazin (collectively these commonly named nematicides are defined as the "Nematicide Group")

Fungicides

Molecules of Formula One may also be used in combination (such as, in a compositional mixture, or a simultaneous or sequential application) with one or more of the following fungicides—(3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfuram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothalisopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, zoxamide (collectively these commonly named fungicides are defined as the "Fungicide Group").

Herbicides

Molecules of Formula One may also be used in combination (such as, in a compositional mixture, or a simultaneous or sequential application) with one or more of the following herbicides—2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlornitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, fluorochloridone, fluoroxypyr, fluoroxypyr-butomethyl, fluoroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluoron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, xylachlor, (collectively these commonly named herbicides are defined as the "Herbicide Group").

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinememafeltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;

3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl)hydrazone;
15. N-ethyl-2,2-dichloro-1-methylcyclopropane-carboxamide-2-(2,6-dichloro-α,α,α-trifluoro-p-tolyl)hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl]phenyl mesylate; and
20. N-Ethyl-2,2-dichloro-1-methylcyclopropanecarboxamide-2-(2,6-dichloro-alpha,alpha,alpha-trifluoro-p-tolyl)hydrazone.

Molecules of Formula One may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, and/or virucides (collectively these commonly named groups are defined as the "AI Group"). It should be noted that compounds falling within the AI Group, Insecticide Group, Fungicide Group, Herbicide Group, Acaricide Group, or Nematicide Group might be in more than one group, because of multiple activities the compound has. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Synergistic Mixtures and Synergists

Molecules of Formula One may be used with the compounds in the Insecticide Group to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs). Additionally, molecules of Formula One may be used with compounds in the Fungicide Group, Acaricide Group, Herbicide Group, or Nematicide Group to form synergistic mixtures. Furthermore, molecules of Formula One may be used with other active compounds, such as the compounds under the heading "OTHER ACTIVE COMPOUNDS", algicides, avicides, bactericides, molluscicides, rodenticides, virucides, herbicide safeners, adjuvants, and/or surfactants to form synergistic mixtures. Generally, weight ratios of the molecules of Formula One in a synergistic mixture with another compound are from about 10:1 to about 1:10, preferably from about 5:1 to about 1:5, and more preferably from about 3:1, and even more preferably about 1:1. Additionally, the following compounds are known as synergists and may be used with the molecules disclosed in Formula One: piperonyl butoxide, piprotal, propyl isome, sesamex, sesamolin, sulfoxide, and tribufos (collectively these synergists are defined as the "Synergists Group").

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus,* and *Pthirus pubis.*

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *Zabrus tenebrioides.*

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis,* and *Supella longipalpa.*

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use aluminum sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP).

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

TABLE 1

| Compound No. | Structure |
|---|---|
| 1 | 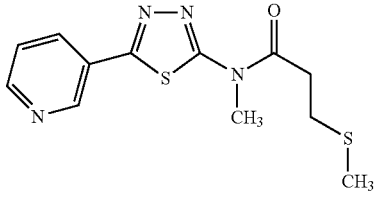 |
| 2 | 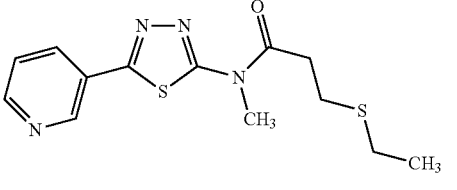 [SMILES: CCSCCC(=O)N(C)c1nnc(-c2cccnc2)s1] |
| 3 | 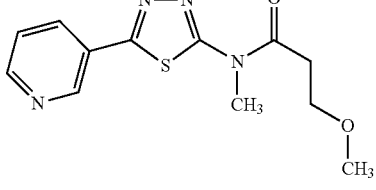 |
| 4 | 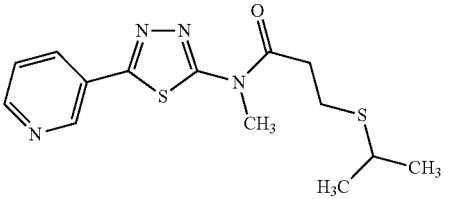 [SMILES: CC(C)SCCC(=O)N(C)c1nnc(-c2cccnc2)s1] |

TABLE 1-continued

| Compound No. | Structure |
|---|---|
| 5 | 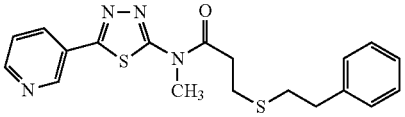 [SMILES: CN(C(=O)CCSCCc1ccccc1)c1nnc(-c2cccnc2)s1] |
| 6 | 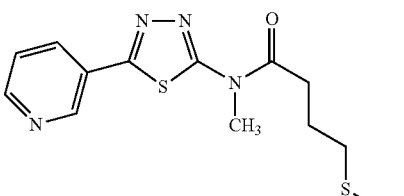 |
| 7 | 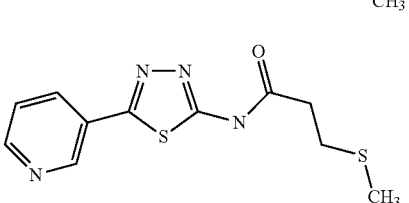 |
| 8 | 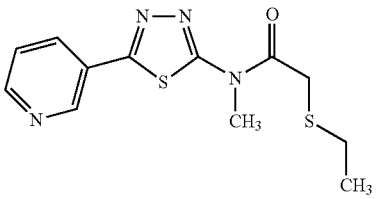 [SMILES: CCSCC(=O)N(C)c1nnc(-c2cccnc2)s1] |
| 9 | 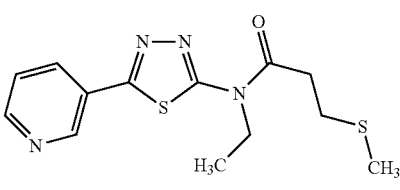 [SMILES: CCN(C(=O)CCSC)c1nnc(-c2cccnc2)s1] |
| 10 | 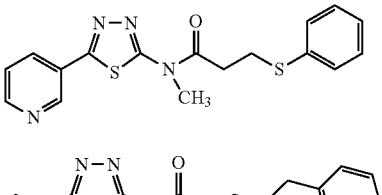 |
| 11 | 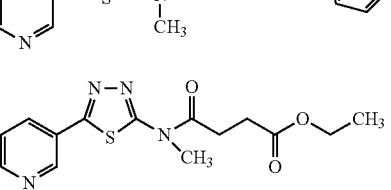 |
| 12 | 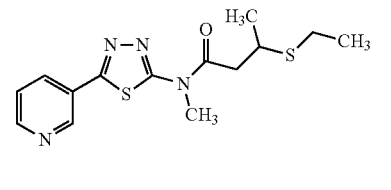 [SMILES: CCSC(C)CC(=O)N(C)c1nnc(-c2cccnc2)s1] |
| 13 | 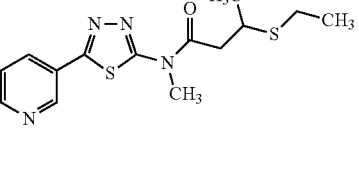 |

TABLE 1-continued

Compound number and structure

| Compound No. | Structure |
|---|---|
| 14 | pyridin-3-yl-1,3,4-thiadiazol-2-yl N(H) C(O)O-ethyl |
| 15 | pyridin-3-yl-1,3,4-thiadiazol-2-yl N(CH3) C(O)O-ethyl |
| 16 | pyridin-3-yl-1,3,4-thiadiazol-2-yl N(CH3) C(O)O-CH2CH2-OCH3 |
| 17 | pyridin-3-yl-1,3,4-thiadiazol-2-yl N(CH3) C(O)-C(CH3)2-CH2-S-ethyl |
| 18 | pyridin-3-yl-1,3,4-thiadiazol-2-yl N(CH3) C(O)-CH2CH2-S(O)-CH3 |
| 19 | pyridin-3-yl-1,3,4-thiadiazol-2-yl N(CH3) C(O)-CH2CH2CH2-OCH3 |
| 20 | pyridin-3-yl-1,3,4-thiadiazol-2-yl N(CH3) C(O)-CH2CH2-S(O)2-CH3 |
| 21 | pyridin-3-yl-1,3,4-thiadiazol-2-yl N(CH3) C(O)-CH=CH-S-CH3 |
| 22 | pyridin-3-yl-1,3,4-thiadiazol-2-yl N(CH3) C(O)-CH2CH2-S-C(C6H5)3 |

TABLE 1-continued

Compound number and structure

| Compound No. | Structure |
|---|---|
| 23 | pyridin-3-yl-1,3,4-thiadiazol-2-yl N(CH3) C(O)-CH2CH2-N3 |
| 24 | pyridin-3-yl-1,3,4-thiadiazol-2-yl N(CH3) C(O)-C(CH3)2-CH2-S-CH3 |
| 25 | pyridin-3-yl-1,3,4-thiadiazol-2-yl N(CH3) C(O)-CH2CH2-SH |
| 26 | pyridin-3-yl-1,3,4-thiadiazol-2-yl N(CH3) C(O)-CH2CH2-S-C(O)CH3 |
| 27 | pyridin-3-yl-1,3,4-thiadiazol-2-yl N(CH3) C(O)-CH2CH2-S-CF3 |
| 28 | pyridin-3-yl-1,3,4-thiadiazol-2-yl N(CH3) C(O)-CH(CH3)-CH2-S-CH3 |
| 29 | pyridin-3-yl-1,3,4-thiadiazol-2-yl N(CH3) C(O)-CH2-S-CH3 |
| 30 | pyridin-3-yl-1,3,4-thiadiazol-2-yl N(CH3) C(O)-CH2-NH-C(O)O-CH2-C6H5 |
| 31 | pyridin-3-yl-1,3,4-thiadiazol-2-yl N(CH3) C(O)-CH2-N(CH3)-C(O)O-CH2-C6H5 |

TABLE 1-continued

Compound number and structure

| Compound No. | Structure |
|---|---|
| 32 | |
| 33 | |
| 34 | |
| 35 | |
| 36 | |
| 37 | |
| 38 | |
| 39 | |
| 40 | |
| 41 | |
| 42 | 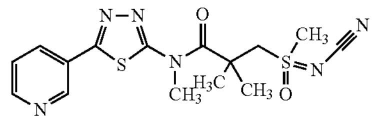 [SMILES: CN(C(=O)C(C)(C)CS(C)(=O)=NC#N)c1nnc(-c2cccnc2)s1] |
| 43 | 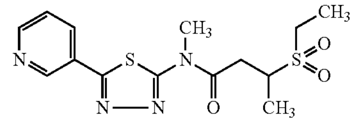 |
| 44 | 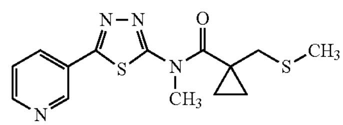 [SMILES: CSCC1(C(=O)N(C)c2nnc(-c3cccnc3)s2)CC1] |
| 45 | 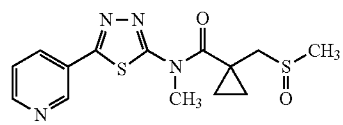 [SMILES: CN(C(=O)C1(CS(C)=O)CC1)c1nnc(-c2cccnc2)s1] |
| 46 | 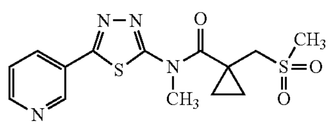 [SMILES: CN(C(=O)C1(CS(C)(=O)=O)CC1)c1nnc(-c2cccnc2)s1] |
| 47 | 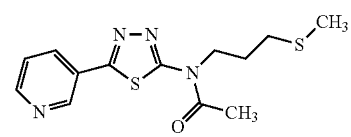 [SMILES: CSCCCN(C(C)=O)c1nnc(-c2cccnc2)s1] |
| 48 | 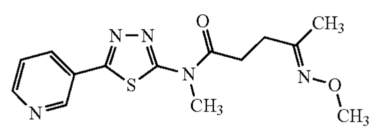 [SMILES: CO/N=C(\C)CCC(=O)N(C)c1nnc(-c2cccnc2)s1] |
| 49 | 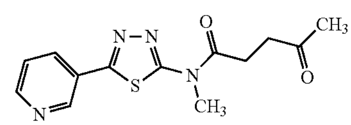 [SMILES: CC(=O)CCC(=O)N(C)c1nnc(-c2cccnc2)s1] |
| 50 | 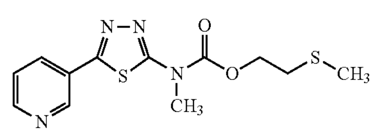 [SMILES: CSCCOC(=O)N(C)c1nnc(-c2cccnc2)s1] |
| 51 | 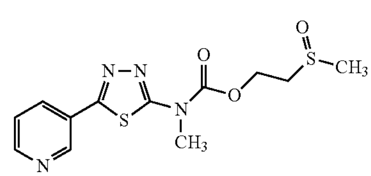 [SMILES: CN(C(=O)OCCS(C)=O)c1nnc(-c2cccnc2)s1] |
| 52 | 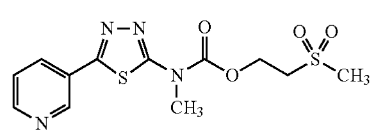 [SMILES: CN(C(=O)OCCS(C)(=O)=O)c1nnc(-c2cccnc2)s1] |

TABLE 1-continued

Compound number and structure

| Compound No. | Structure |
|---|---|
| 53 | |
| 54 | |
| 55 | |
| 56 | |
| 57 | |
| 58 | |
| 59 | |
| 60 | |
| 61 | |
| 62 | 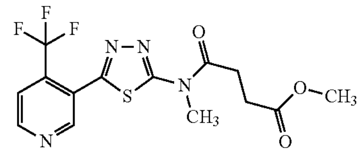 [SMILES: COC(=O)CCC(=O)N(C)c1nnc(-c2cnccc2C(F)(F)F)s1] |
| 63 | 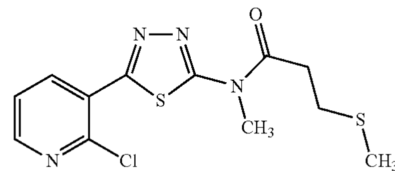 [SMILES: CSCCC(=O)N(C)c1nnc(-c2cccnc2Cl)s1] |
| 64 | 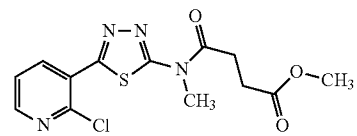 [SMILES: COC(=O)CCC(=O)N(C)c1nnc(-c2cccnc2Cl)s1] |
| 65 | 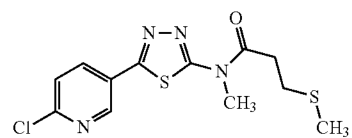 |
| 66 | 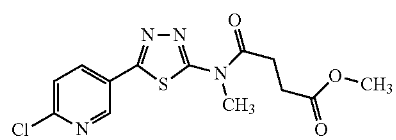 [SMILES: COC(=O)CCC(=O)N(C)c1nnc(-c2ccc(Cl)nc2)s1] |
| 67 | 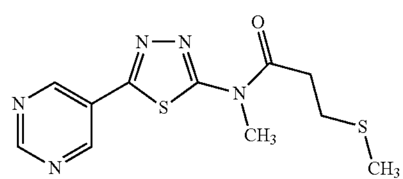 [SMILES: CSCCC(=O)N(C)c1nnc(-c2cncnc2)s1] |
| 68 | 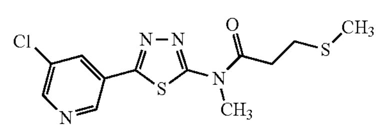 [SMILES: CSCCC(=O)N(C)c1nnc(-c2cncc(Cl)c2)s1] |
| 69 | 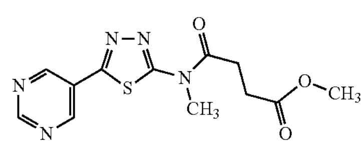 [SMILES: COC(=O)CCC(=O)N(C)c1nnc(-c2cncnc2)s1] |
| 70 | 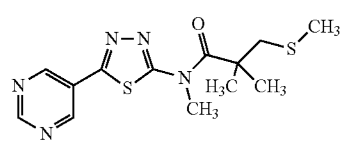 [SMILES: CSCC(C)(C)C(=O)N(C)c1nnc(-c2cncnc2)s1] |
| 71 | 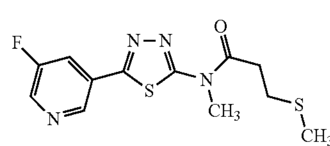 [SMILES: CSCCC(=O)N(C)c1nnc(-c2cncc(F)c2)s1] |

TABLE 1-continued
Compound number and structure
| Compound No. | Structure |
|---|---|
| 72 | 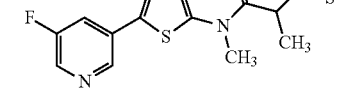 |
| 73 | 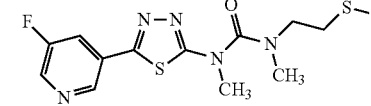 |
| 74 | 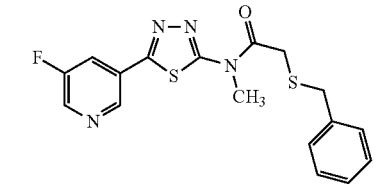 [SMILES: CN(C(=O)CSCc1ccccc1)c1nnc(-c2cncc(F)c2)s1] |
| 75 | 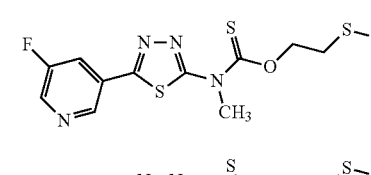 |
| 76 | 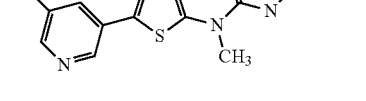 |
| 77 | 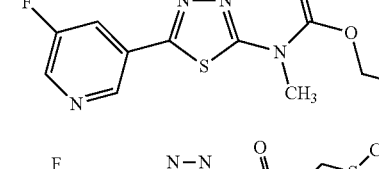 |
| 78 | 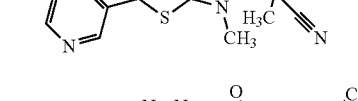 |
| 79 | 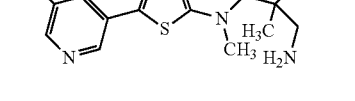 |
| 80 | 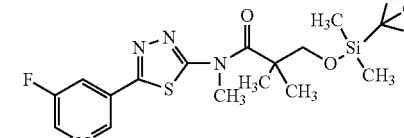 |
| 81 | 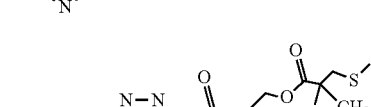 |
| 82 | |
| 83 | |
| 84 | |
| 85 | |
| 86 | |
| 87 | |
| 88 | |
| 89 | |
| 90 | |
| 91 | |

TABLE 1-continued

Compound number and structure

| Compound No. | Structure |
|---|---|
| 92 | [pyridin-3-yl-1,3,4-thiadiazol-2-yl amide with CH(CH3)CH2SCH3 group] |
| 93 | [pyridin-3-yl-1,3,4-thiadiazol-2-yl amide with CH(CH3)CH2S-allyl group] |
| 94 | [pyridin-3-yl-1,3,4-thiadiazol-2-yl N-methyl amide with CH(CH3)CH2S-allyl group] |
| 95 | [pyridin-3-yl-1,3,4-thiadiazol-2-yl N-methyl thiourea with NHCH2CH2OCH3] |
| 96 | [pyridin-4-yl-1,3,4-thiadiazol-2-yl N-methyl amide with CH2CH2SCH3] |
| 97 | [pyridin-4-yl-1,3,4-thiadiazol-2-yl N-methyl amide with CH2CH2C(O)OCH3] |
| 98 | [pyridin-3-yl-1,3,4-thiadiazol-2-yl N-cyclopropylmethyl amide with CH2CH2SCH3] |

TABLE 2

Analytical Data

| Compound No. | Appearance | mp (° C.) | IR (KBr thin film) cm$^{-1}$ | MS (ESIMS m/z) | $^1$H NMR |
|---|---|---|---|---|---|
| 1 | yellow solid | 99-101 | | 295.12 | |
| 2 | white solid | 70-72 | | 310.1 (M + 2) | |
| 3 | white solid | 92-97.5 | | 279.1 | |
| 4 | white solid | 100-105 | | | |
| 5 | white solid | 105-108 | | 385.5 | |
| 6 | tan solid | 93-95 | | 309.4 | |
| 7 | light brown solid | 211-212 | | | |
| 8 | pale yellow solid | 87-92 | | 294.7 | |
| 9 | tan solid | 116-120 | | 308.7 | |
| 10 | yellow film | | | | (300 MHz, CDCl$_3$) δ 9.19 (br s, 1H), 8.74 (br s, 1H), 8.30 (br d, J = 8 Hz, 1H), 7.20-7.50 (m, 6H), 3.80 (s, 3H), 3.37 (t, J = 7 Hz, 2H), 3.03 (t, J = 7 Hz, 2H). |
| 11 | cream solid | 116-118 | | 371.19 | |
| 12 | light brown crystals | 137-139 | | 321.02 | |
| 13 | brown paste | | | 323.02 | (300 MHz, CDCl$_3$) δ 9.15 (br d, J = 2 Hz, 1H), 8.70 (dd, J = 2.5 Hz, 1H), 8.30 (m, 1H), 7.43 (dd, J = 5.8 Hz, 1H), 3.87 (s, 3H), 2.60-3.50 (m, 5H), 1.42 (d, J = 7 Hz, 3H), 1.26 (t, J = 7 Hz, 3H). |
| 14 | cream powder | 127-132 | | 251.11 | |
| 15 | tan powder | 162-164 | | | |
| 16 | white film | | | 295.16 | (300 MHz, CDCl$_3$) δ 9.10 (br s, 1H), 8.68 (br s, 1H), 8.25 (m, 1H), 7.40 (m, 1H), 4.48 (m, 2H), 3.71 (m, 5H), 3.42 (s, 3H). |

TABLE 2-continued

Analytical Data

| Compound No. | Appearance | mp (° C.) | IR (KBr thin film) cm$^{-1}$ | MS (ESIMS m/z) | $^1$H NMR |
|---|---|---|---|---|---|
| 17 | yellow oil | | | 337.12 | (300 MHz, CDCl$_3$) δ 9.15 (d, J = 2 Hz, 1H), 8.68 (dd, J = 2.5 Hz, 1H), 8.27 (dt, J = 2.8 Hz, 1H), 7.41 (dd, J = 5.8 Hz, 1H), 3.97 (s, 3H), 2.98 (s, 2H), 2.58 (q, J = 7 Hz, 2H), 1.55 (s, 6H), 1.25 (t, J = 7 Hz, 3H). |
| 18 | off-white powder | 138-140 | | 310.93 | |
| 19 | light brown solid | 92-95 | | 293.2 | |
| 20 | white powder | 199-201 | | 292.96 | |
| 21 | white powder | | | 292.96 | (300 MHz, (CD$_3$)$_2$SO) δ 9.14 (br s, 1H), 8.67 (m, 1H), 8.27 (m, 1H), 8.11 (d, J = 14 Hz, 1H), 7.41 (m, 1H), 6.30 (d, J = 14 Hz, 1H), 3.91 (s, 3H), 2.46 (s, 3H). |
| 22 | white foam | 60-75 | | 523.18 | |
| 23 | white solid | 155-159 | | 288 | |
| 24 | pale yellow crystals | 89-91 | | 323.21 | |
| 25 | white powder | 149-151 | | 281.16 | |
| 26 | white powder | 133-135 | | 323.14 | |
| 27 | pale yellow film | | | 349.12 | (300 MHz, CDCl$_3$) δ 9.15 (d, J = 2 Hz, 1H), 8.70 (dd, J = 2.5 Hz, 1H), 8.28 (dt, J = 2.8 Hz, 1H), 7.43 (dd, J = 5.8 Hz, 1H), 3.86 (s, 3H), 3.30 (t, J = 7 Hz, 2H), 3.16 (t, J = 7 Hz, 2H). |
| 28 | brown semi-solid | | | 309.2 | (300 MHz, CDCl$_3$) δ 9.15 (d, J = 2 Hz, 1H), 8.69 (dd, J = 2.5 Hz, 1H), 8.28 (dt, J = 2.8 Hz, 1H), 7.42 (dd, J = 5.8 Hz, 1H), 3.94 (s, 3H), 3.33 (m, 1H), 3.01 (dd, J = 8.13 Hz, 1H), 2.69 (dd, J = 6.13 Hz, 1H), 2.15 (s, 3H), 1.37 (d, J = 7 Hz, 3H). |
| 29 | tan solid | 135-139 | | 281.18 | |
| 30 | pale yellow foam | | | 398.05 | (300 MHz, CDCl$_3$) δ 9.14 (d, J = 2 Hz, 1H), 8.70 (dd, J = 2.5 Hz, 1H), 8.28 (dt, J = 2.8 Hz, 1H), 7.31-7.45 (m, 6H), 5.45 (br s, 1H), 5.10 (s, 2H), 3.82 (s, 3H), 3.65 (m, 2H), 2.94 (m, 2H). |
| 31 | off-white semisolid | | | 412.06 | (300 MHz, CDCl3) δ 9.14 (d, J = 2 Hz, 1H), 8.70 (dd, J = 2.5 Hz, 1H), 8.28 (dt, J = 2.8 Hz, 1H), 7.31-7.45 (m, 6H), 5.14 (br s, 2H), 3.67-3.87 (m, 5H), 2.85-3.08 (m, 5H). |
| 32 | brown oil | | | 339 | (300 MHz, CDCl3) δ 9.13 (m, 1H), 8.69 (dd, 1H, J = 2.5 Hz), 8.28 (m, 1H), 7.42 (ddd, 1H, J = 1, 5.8 Hz), 3.98 (s, 3H), 3.50 (d, 1H, J = 13 Hz), 2.81 (d, 1H, J = 13 Hz), 2.78 (s, 3H), 1.83 (s, 3H), 1.64 (s, 3H). |
| 33 | white crystals | | | 355 | (300 MHz, CDCl3) δ 9.14 (br s, 1H), 8.70 (br s, 1H), 8.29 (m, 1H), 7.43 (m, 1H), 3.98 (s, 3H), 3.64 (s, 2H), 3.09 (s, 3H), 2.78 (s, 3H), 1.74 (s, 6H). |
| 34 | tan powder | 121-123 | | 236.04 | |
| 35 | pale yellow powder | 182-188 | | 309.2 | |

TABLE 2-continued

Analytical Data

| Compound No. | Appearance | mp (° C.) | IR (KBr thin film) cm$^{-1}$ | MS (ESIMS m/z) | $^1$H NMR |
|---|---|---|---|---|---|
| 36 | white powder | | | 341.18 | (300 MHz, CDCl3) δ 10.48 (br s, 1H), 9.14 (br s, 1H), 8.72 (m, 1H), 8.27 (m, 1H), 7.45 (m, 1H), 3.65 (s, 2H), 2.99 (s, 3H), 1.69 (s, 6H). |
| 37 | pale yellow film | | | 340.99 | (300 MHz, CDCl3) δ 9.14 (br s, 1H), 8.71 (br s, 1H), 8.29 (d, J = 8 Hz, 1H), 7.42 (br s, 1H), 3.79-4.01 (m, 5H), 3.16 (dd, J = 3.13 Hz, 1H), 2.96 (s, 3H), 1.43 (d, J = 7 Hz, 3H). |
| 38 | tan foam | 41-48 | | 364.08 | |
| 39 | off-white foam | 42-52 | | 326.9 | |
| 40 | white powder | 198-201 | | 403 | |
| 41 | tan powder | 110-112 | | 264.1 | |
| 42 | white foam | | | 379.19 | (300 MHz, CDCl$_3$) δ 9.12 (br s, 1H), 8.70 (d, J = 4 Hz, 1H), 8.29 (dt, J = 2.8 Hz, 1H), 7.43 (dd, J = 8.5 Hz, 1H), 4.21 (d, J = 15 Hz, 1H), 3.97 (s, 3H), 3.69 (d, J = 15 Hz, 1H), 3.53 (s, 3H), 1.92 (s, 3H), 1.63 (s, 3H). |
| 43 | white solid | 175-177 | | 355 | |
| 44 | tan powder | 144-147 | | 321.03 | |
| 45 | white powder | 166-168 | | 337 | |
| 46 | white powder | 208-212 | | 353 | |
| 48 | Yellow amorphous solid | 114-121 | | 320.1 | |
| 49 | Yellow needles | 146-147 | | 291.16 | |
| 50 | white powder | 126-128 | | 311.12 | |
| 51 | white powder | 170-172 | | 327 | |
| 52 | white powder | 198-200 | | 343 | |
| 53 | yellow oil | | | 351.23 | (300 MHz, CDCl3) δ 8.98 (d, J = 2 Hz, 1H), 8.75 (dd, J = 2.5 Hz, 1H), 7.99 (dt, J = 2.8 Hz, 1H), 7.46 (dd, J = 5.8 Hz, 1H), 3.32 (s, 3H), 3.11 (s, 2H), 2.12 (s, 3H), 1.96-2.11 (m, 4H), 0.84 (t, J = 7 Hz, 6H). |
| 54 | yellow film | | | 282 (M − Me) | (300 MHz, CDCl3) δ 8.89 (br s, 1H), 8.64 (br s, 1H), 7.97 (dt, J = 2.8 Hz, 1H), 7.37 (dd, J = 5.8 Hz, 1H), 5.12 (s, 2H), 3.14 (s, 3H), 2.32 (s, 3H). |
| 55 | off-white powder | 192-194 | | 267.1 | |
| 56 | off-white powder | 152-154 | | 307 | |
| 57 | yellow oil | | | 385 | (300 MHz, CDCl$_3$) δ 9.15 (d, J = 2 Hz, 1H), 8.70 (dd, J = 2.5 Hz, 1H), 8.28 (dt, J = 2.8 Hz, 1H), 7.42 (dd, J = 5.8 Hz, 1H), 7.11-7.28 (m, 5H), 3.52-3.61 (m, 4H), 2.98-3.07 (m, 3H), 2.82 (dd, J = 5.13 Hz, 1H), 2.13 (s, 3H). |
| 58 | tan film | 117-120 | | 357.18 | |
| 59 | brown powder | 152-155 | | 369.2 | |
| 60 | yellow film | | | 363 | (300 MHz, CDCl$_3$) δ 8.96 (s, 1H), 8.92 (d, J = 5 Hz, 1H), 7.71 (d, J = 5 Hz, 1H), 3.90 (s, 3H), 2.90-3.05 (m, 4H), 2.20 (s, 3H). |

TABLE 2-continued

Analytical Data

| Compound No. | Appearance | mp (° C.) | IR (KBr thin film) cm$^{-1}$ | MS (ESIMS m/z) | $^1$H NMR |
|---|---|---|---|---|---|
| 61 | yellow film | | | 375 | (300 MHz, CDCl$_3$) δ 8.95 (s, 1H), 8.92 (d, J = 5 Hz, 1H), 7.71 (d, J = 5 Hz, 1H), 3.93 (s, 3H), 3.74 (s, 3H), 3.04 (t, J = 7 Hz, 2H), 2.83 (t, J = 7 Hz, 2H). |
| 62 | tan powder | 137-140 | | 328.9 | |
| 63 | off-white powder | 130-132 | | 341 | |
| 64 | off-white powder | 153-155 | | 328.9 | |
| 65 | off-white powder | 176-178 | | 341 | |
| 66 | tan powder | 99-102 | | 296 | |
| 67 | Yellowish solid | | 1674 | 329 | |
| 68 | off-white powder | 177-180 | | 308 | |
| 69 | pale yellow film | | | 323.94 | (300 MHz, CDCl$_3$) δ 9.29 (s, 1H), 9.27 (s, 2H), 4.00 (s, 3H), 2.98 (s, 2H), 2.18 (s, 3H), 1.57 (s, 6H). |
| 70 | yellow solid | 108-110 | | 312.39 | |
| 71 | yellow solid | 165-167 | | 338.45 | |
| 72 | yellow solid | 163 | | 309.41 | |
| 73 | yellow oil | | | 340.44 | |
| 74 | dark oil | | | 336.48 | |
| 75 | yellow solid | 114-115 | | 390.45 | |
| 76 | white solid | 169-175 | | 372.44 | |
| 77 | white solid | 135-137 | | 356.44 | |
| 78 | Yellowish solid | 104-106 | | 329.1 | |
| 79 | White solid | 100-104 | | 328.1 | |
| 80 | White solid | 137-140 | | 299.1 | |
| 81 | tan solid | 74-76 | | 326.41 | |
| 83 | Colorless gum | | 1658 | 342.2 | |
| 84 | light brown solid | 145-147 | | 374.46 | |
| 85 | Yellow solid | 150-152 | | 345.1 | |
| 86 | Brown glass | | 1478 | 344.1 | |
| 87 | White solid | | | 283.1 | (CDCl$_3$, 400 MHz) δ ppm 8.90 (br s, 1H), 8.55 (br s, 1H), 8.05 (ddd, J = 8.9, 2.6, 1.6 Hz, 1H), 4.42 (q, J = 7.1 Hz, 2H), 3.73 (s, 3H), 1.43 (t, J = 7.4 Hz, 3H). |
| 88 | Beige solid | 109-111 | 1665 | 352.1 | |
| 89 | Beige solid | 154-157 | | 356.2 | (CDCl$_3$, 400 MHz) δ ppm 11.17 (br, 1H), 9.02 (t, J = 1.6 Hz, 1H), 8.43 (d, J = 2.8 Hz, 1H), 8.11 (ddd, J = 9.8, 2.8, 1.8 Hz, 1H), 3.87 (d, J = 2.9 Hz, 1H), 3.48 (s, 3H), 3.47 (d, J = 2.9 Hz, 1H), 2.99 (d, J = 12.7 Hz, 1H), 2.78 (d, J = 13.6 Hz, 1H), 2.20 (s, 3H), 1.41 (s, 3H). |
| 90 | white solid | 102-105 | 1654 | 425.3 | |
| 91 | white solid | 90-93 | 1724, 1644 | 441.2 | |
| 92 | Yellow solid | 176 | 1694 | 295.45 | |
| 93 | Yellow solid | 143-147 | 1691 | 322.37 | |
| 94 | Waxy white solid | 43-46 | 1667 | 336.52 | |
| 95 | Yellow solid | 118-121 | 1571 | 310.7 | |
| 96 | tan powder | 152-154 | 1667 | | (CDCl$_3$, 300 MHz) δ ppm 8.84 (br s, 2H), 7.86 (m, 2H), 3.88 (s, 3H), 2.91-3.06 (m, 4H), 2.20 (s, 3H). |
| 97 | brown powder | 175-177 | 1725, 1667 | 307.0 | |

TABLE 2-continued

Analytical Data

| Compound No. | Appearance | mp (° C.) | IR (KBr thin film) cm$^{-1}$ | MS (ESIMS m/z) | $^1$H NMR |
|---|---|---|---|---|---|
| 98 | yellow gum | | 1666, 1436 | 334.1 | (400 MHz, CDCl$_3$) δ 9.16 (d, J = 1.5 Hz, 1H), 8.70 (d, J = 3.5 Hz, 1H), 8.28 (dt, J = 7.9, 2.0 Hz, 1H), 7.42 (ddd, J = 8.0, 4.8, 0.6 Hz, 1H), 4.31 (d, J = 6.9 Hz, 2H), 3.11-3.03 (m, 2H), 3.01-2.92 (m, 2H), 2.20 (s, 3H), 1.37-1.26 (m, 1H), 0.67-0.61 (m, 2H), 0.61-0.55 (m, 2H). |

TABLE 3

Biological Data.

| Compound No. | APHIGO % Ctrl @ 200 ppm | MYZUPE % Ctrl @ 200 ppm | BEMITA % Ctrl @ 200 ppm |
|---|---|---|---|
| 1 | A | A | B |
| 2 | A | A | B |
| 3 | A | A | B |
| 4 | A | A | B |
| 5 | B | B | B |
| 6 | A | A | B |
| 7 | B | B | B |
| 8 | A | A | D |
| 9 | A | A | B |
| 10 | B | A | C |
| 11 | B | B | B |
| 12 | A | B | B |
| 13 | A | A | B |
| 14 | B | D | C |
| 15 | B | D | C |
| 16 | A | B | C |
| 17 | A | A | B |
| 18 | A | A | B |
| 19 | A | B | B |
| 20 | A | A | B |
| 21 | B | A | C |
| 22 | D | B | C |
| 23 | A | A | C |
| 24 | A | A | B |
| 25 | A | A | C |
| 26 | B | B | C |
| 27 | A | B | C |
| 28 | A | A | B |
| 29 | A | A | B |
| 30 | B | D | C |
| 31 | D | D | C |
| 32 | A | A | A |
| 33 | A | A | B |
| 34 | D | D | C |
| 35 | A | B | C |
| 36 | A | B | C |
| 37 | A | A | B |
| 38 | A | A | B |
| 39 | A | A | B |
| 40 | D | D | C |
| 41 | A | B | C |
| 42 | B | A | B |
| 43 | A | B | D |
| 44 | A | A | D |
| 45 | A | A | B |
| 46 | A | C | B |
| 47 | B | D | C |
| 48 | A | A | B |
| 49 | A | B | B |
| 50 | A | A | B |
| 51 | A | A | B |
| 52 | B | B | C |
| 53 | A | B | B |
| 54 | B | D | C |
| 55 | B | D | C |
| 56 | A | B | D |
| 57 | B | B | C |
| 58 | D | C | C |
| 59 | B | D | C |
| 60 | B | D | C |
| 61 | A | B | B |
| 62 | B | B | C |
| 63 | B | B | D |
| 64 | D | C | C |
| 65 | B | B | B |
| 66 | B | C | C |
| 67 | A | A | D |
| 68 | B | B | B |
| 69 | B | B | C |
| 70 | A | B | B |
| 71 | C | A | B |
| 72 | C | B | C |
| 73 | C | B | C |
| 74 | C | A | B |
| 75 | C | A | B |
| 76 | C | B | B |
| 77 | C | A | B |
| 78 | C | A | A |
| 79 | C | A | B |
| 80 | C | A | B |
| 81 | C | B | B |
| 83 | C | A | B |
| 84 | C | B | B |
| 85 | C | B | B |
| 86 | C | A | A |
| 87 | C | C | A |
| 88 | C | A | B |
| 89 | C | B | B |
| 90 | C | C | C |
| 91 | C | A | A |
| 92 | C | B | B |
| 93 | C | A | B |
| 94 | C | A | A |
| 95 | C | A | B |
| 96 | B | C | C |
| 97 | B | D | C |
| 98 | C | A | D |

| MYZUPE, APHIGO and BEMITA Rating Table | |
|---|---|
| % Control (or Mortality) | Rating |
| 80-100 | A |
| More than 0-Less than 80 | B |
| Not Tested | C |
| No activity noticed in this bioassay | D |

We claim:
1. A molecule according to Formula One:

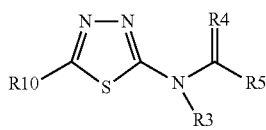

Formula One wherein
R10 is

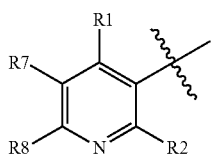

R1 is H, F, Cl, Br, I, or substituted or unsubstituted $C_1$-$C_6$ alkyl, wherein each said R1, which is substituted, has one or more substituents selected from F, Cl, Br, or I;
R2 is selected from H, F, Cl, Br, I, or substituted or unsubstituted $C_1$-$C_6$ alkyl, wherein each said R2, which is substituted, has one or more substituents selected from F, Cl, Br, or I;
R3 is H or substituted or unsubstituted $C_1$-$C_6$ alkyl;
R4 is O or S;
R5 is
($C_1$-$C_{12}$ alkyl)C(=NO($C_1$-$C_{12}$ alkyl))($C_1$-$C_{12}$ alkyl),
($C_1$-$C_{12}$ alkyl)N(R9)$_2$,
($C_1$-$C_{12}$ alkyl)N(R9)C(=O)O($C_1$-$C_{12}$ alkyl),
($C_1$-$C_{12}$ alkyl)O($C_1$-$C_{12}$ alkyl),
($C_1$-$C_{12}$ alkyl)S(O)$_n$(=NCN)($C_1$-$C_{12}$ alkyl),
($C_1$-$C_{12}$ alkyl)S(O)$_n$R6, or
O($C_1$-$C_{12}$ alkyl)S(O)$_n$($C_1$-$C_{12}$ alkyl);
R6 is H;
R7 is H, F, Cl, Br, I, or substituted or unsubstituted $C_1$-$C_6$ alkyl;
R8 is H, F, Cl, Br, I, or substituted or unsubstituted $C_1$-$C_6$ alkyl;
R9 (each independently) is H or substituted or unsubstituted $C_1$-$C_6$ alkyl, wherein each said R9, which is substituted, has one or more substituents selected from F, Cl, Br, I, CN, or $NO_2$; and
n is (each independently) 0, 1, or 2.

2. A process comprising applying a molecule according to claim 1 to an area to control a pest in an amount sufficient to control such pest.

3. A molecule that is a pesticidally acceptable acid addition salt, a salt derivative, a solvate, or an ester derivative, of a molecule according to claim 1.

4. A molecule according to claim 1 wherein at least one H is $^2$H or at least one C is $^{14}$C.

5. A composition comprising a molecule according to claim 1 and at least one other compound selected from the Insecticide Group, Acaricide Group, Nematicide Group, Fungicide Group, Herbicide Group, AI Group, or Synergist Group.

6. A composition comprising a molecule according to claim 1 and at least one other compound selected from the Insecticide Group, Acaricide Group, Nematicide Group, Fungicide Group, Herbicide Group, AI Group, or Synergist Group.

7. A composition comprising a molecule according to claim 1 and a seed.

8. A composition according to claim 1 wherein said seed has been genetically modified to express one or more specialized traits.

9. A process comprising: orally administering; or topically applying; a molecule according to claim 1, to a non-human animal, to control endoparasites, ectoparasites, or both.

10. A molecule according to claim 1 having one of the following structures

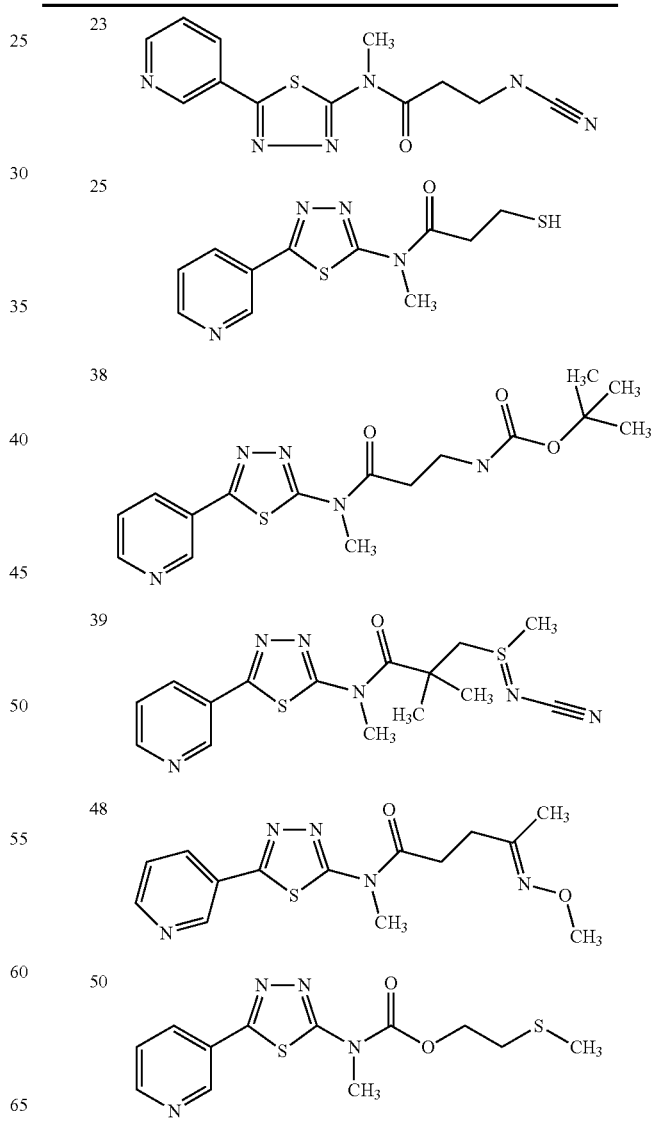

| 51 | 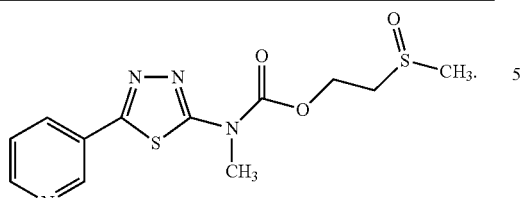 |
|---|---|
* * * * *